(12) United States Patent
Poulos et al.

(10) Patent No.: US 9,068,280 B2
(45) Date of Patent: Jun. 30, 2015

(54) DROPLET BILAYER FORMATION USING THROUGHPUT LIQUID HANDLING TECHNIQUES

(75) Inventors: Jason L. Poulos, Los Angeles, CA (US); Jacob J. Schmidt, Sherman Oaks, CA (US)

(73) Assignee: The Regents of the University of California, Oakland, CA (US)

( * ) Notice: Subject to any disclaimer, the term of this patent is extended or adjusted under 35 U.S.C. 154(b) by 545 days.

(21) Appl. No.: 13/520,339

(22) PCT Filed: Jan. 5, 2011

(86) PCT No.: PCT/US2011/020284
§ 371 (c)(1),
(2), (4) Date: Nov. 14, 2012

(87) PCT Pub. No.: WO2011/085047
PCT Pub. Date: Jul. 14, 2011

(65) Prior Publication Data
US 2013/0056358 A1    Mar. 7, 2013

Related U.S. Application Data

(60) Provisional application No. 61/292,361, filed on Jan. 5, 2010.

(51) Int. Cl.
*G01N 3/02*    (2006.01)
*C40B 50/08*    (2006.01)
(Continued)

(52) U.S. Cl.
CPC .................. *C40B 50/08* (2013.01); *C40B 40/14* (2013.01); *G01N 33/48728* (2013.01)

(58) Field of Classification Search
CPC .................... G01N 33/48728; G01N 27/00
USPC .................................... 324/693, 71.1
See application file for complete search history.

(56) References Cited

U.S. PATENT DOCUMENTS 3,846,795 A    11/1974 Jones
6,436,905 B1    8/2002 Tonge et al.
6,682,893 B2    1/2004 Taylor et al.
(Continued)

FOREIGN PATENT DOCUMENTS

EP    2293921 A1    3/2011
EP    2521650 A1    11/2012
(Continued)

OTHER PUBLICATIONS

Alvarez O, et al. "How to set up a bilayer system. In Ion Channel Reconstitution." ed.; Miller, C., Ed. Plenum Press: New York, 1986: 115-139.
(Continued)

*Primary Examiner* — Vincent Q Nguyen
(74) *Attorney, Agent, or Firm* — Ballard Spahr LLP

(57) ABSTRACT

The invention relates to methods and devices for forming and measuring lipid bilayers, for example, by joining lipid monolayers that self-assemble at the interface of aqueous and organic phases using sessile aqueous droplets in contact with a measurement electrode. At least one of the aqueous solution, the lower aqueous phase, and/or the upper organic phase comprise lipids. This abstract is intended as a scanning tool for purposes of searching in the particular art and is not intended to be limiting of the present invention.

19 Claims, 6 Drawing Sheets

(51) Int. Cl.
*C40B 40/14* (2006.01)
*G01N 33/487* (2006.01)

(56) References Cited

U.S. PATENT DOCUMENTS

| | | | |
|---|---|---|---|
| 6,699,952 B2 | 3/2004 | Chaikof et al. |
| 6,846,352 B2 | 1/2005 | Yatake |
| 6,846,795 B2 | 1/2005 | Lant et al. |
| 6,849,426 B2 | 2/2005 | Chen et al. |
| 6,852,816 B2 | 2/2005 | Lewis et al. |
| 6,913,697 B2 | 7/2005 | Lopez et al. |
| 7,201,836 B2 | 4/2007 | Vogel et al. |
| 7,479,483 B2 | 1/2009 | Ponzoni et al. |
| 7,638,092 B2 | 12/2009 | Ide |
| 8,038,885 B2 | 10/2011 | Schmidt et al. |
| 8,242,077 B2 | 8/2012 | Lakey et al. |
| 2002/0081617 A1 | 6/2002 | Buranda et al. |
| 2003/0096418 A1 | 5/2003 | Yamazaki et al. |
| 2003/0175824 A1 | 9/2003 | Pishko et al. |
| 2005/0112184 A1 | 5/2005 | Jahn et al. |
| 2005/0154374 A1 | 7/2005 | Hunter et al. |
| 2006/0003097 A1 | 1/2006 | Andres et al. |
| 2006/0029955 A1 | 2/2006 | Guia et al. |
| 2006/0094119 A1 | 5/2006 | Ismagilov et al. |
| 2006/0160066 A1 | 7/2006 | Bhatia et al. |
| 2009/0170118 A1 | 7/2009 | Schmidt et al. |
| 2011/0111985 A1 | 5/2011 | Lakey et al. |
| 2011/0118489 A1 | 5/2011 | Schmidt et al. |
| 2012/0025414 A1 | 2/2012 | Schmidt et al. |
| 2013/0147461 A1 | 6/2013 | Schmidt et al. |

FOREIGN PATENT DOCUMENTS

| | | |
|---|---|---|
| EP | 2578207 A2 | 4/2013 |
| WO | WO-01/20330 A1 | 3/2001 |
| WO | WO-03/086197 A1 | 10/2003 |
| WO | WO-2007/028003 A2 | 3/2007 |
| WO | WO-2007/047498 A2 | 4/2007 |
| WO | WO-2009/143425 A1 | 11/2009 |
| WO | WO-2011/085047 A1 | 7/2011 |

OTHER PUBLICATIONS

Cleveland PH, et al. "Nanoliter dispensing for uHTS using pin tools." Assay and Drug Development Technologies 2005, 3(2): 213-225.
Koper I. "Insulating tethered bilayer lipid membranes to study membrane proteins." Molecular BioSystems, 2007, 3: 651-657.
Krylov et al., "Water Permeability of Asymmetric Planar Lipid Bilayers—Leaflets of Different Composition Offer Independent and Additive Resistances to Permeation." JPG 2001, 118(4):333-340.
Mueller et al., "Reconstitution of excitable cell membrane structure in vitro," Circulation 1962, 26:1167-1171.
Portonovo SA, et al. "hERG Drug response measured in droplet bilayers."
Rossi C and Chopineau J. Biomimetic tethered lipid membranes designed for membrane-protein interaction studies. Eur Biophys J 2007, 36(8): 955-965.
Strauss G and Hauser H. "Stabilization of lipid bilayer vesicles by sucrose during freezing." Proc Natl Acad Sci USA 1986, 83(8): 2422-2426.
Tanaka M and Sackmann E. "Polymer-supported membranes as models of the cell surface". Nature, 2005, 437, 656-663.
White SH, et al. "Formation of planar bilayer membranes from lipid monolayers." Biophysical Journal 1976, 16: 481-489.
Examiner Interview Summary issued Jun. 16, 2011 for U.S. Appl. No. 12/083,410, filed Jun. 2, 2008 (Inventors—Schmidt, et al.) (2 pages).
Examiner's Amendment issued Jun. 16, 2011 for U.S. Appl. No. 12/083,410, filed Jun. 2, 2008 (Inventors—Schmidt, et al.) (6 pages).
Petition for Review filed Aug. 1, 2011 for U.S. Appl. No. 12/083,410, filed Jun. 2, 2008 (Inventors—Schmidt, et al.) (2 pages).
Notice of Allowance issued Aug. 4, 2011 for U.S. Appl. No. 12/083,410, filed Jun. 2, 2008 (Inventors—Schmidt, et al.) (2 pages).
Petition Decision issued Sep. 1, 2011 for U.S. Appl. No. 12/083,410, filed Jun. 2, 2008 (Inventors—Schmidt, et al.) (1 page).
Response to Non-Final Office Action filed Apr. 30, 2014 for U.S. Appl. No. 13/269,433, filed Oct. 7, 2011 (Inventors—Schmidt, et al.) (11 pages).
Final Office Action issued Jun. 18, 2014 for U.S. Appl. No. 13/269,433, filed Oct. 7, 2011 (Inventors—Schmidt, et al.) (8 pages).
Response filed Oct. 7, 2013 for U.S. Appl. No. 12/993,713, filed May 22, 2009 (Inventors—Schmidt, et al.) (10 pages).
Notice of Allowance issued Jun. 16, 2011 for U.S. Appl. No. 12/993,713, filed May 22, 2009 (Inventors—Schmidt, et al.) (8 pages).
Preliminary Amendment filed Jun. 16, 2014 for U.S. Appl. No. 14/306,050, filed Jun. 16, 2014 (Inventors—Schmidt, et al.) (10 pages).
Non-Final Office Action issued Oct. 29, 2014 for U.S. Appl. No. 13/646,305, filed Oct. 5, 2012 (Inventors—Schmidt, et al.) (11 pages).
Communication Pursuant to Rules 161(2) and 162 EPC issued Jan. 14, 2011 for European Application No. 09751653.8, which is a national phase of PCT/US2009/044979, filed 05/22/09 and later published as WO 2009/143425 on Nov. 26, 2009 (Applicant—The Regents of the University of California // Inventors—Jacob J. Schmidt, et al.) (2 pages).
Communication Pursuant to Rules 161(2) and 162 EPC issued Aug. 14, 2012 for European Application No. 11732112.5, which is a national phase of PCT/US2011/020284, filed Jan. 5, 2011 and later published as WO 2011/085047 on Jul. 14, 2011 (Applicant—The Regents of the University of California // Inventors—Jason L. Poulos, et al.) (2 pages).
European Search Report issued Apr. 16, 2013 for European Patent Application EP 2521650 filed May 22, 2009 (Applicant—The Regents of the University of California // Inventors—Schmidt, et al.) (4 pages).
Voluntary Amendment filed Nov. 7, 2012 for European Application No. 12006905.9 filed on Oct. 5, 2012, which claims priority to U.S. Appl. No. 61/543,771 (Applicant—The Regents of the University of California // Inventors—Schmidt, et al.) (16 pages).
Voluntary Amendment filed Dec. 22, 2010 for European Application No. 09751653.8, which is a national phase of PCT/US2009/044979, filed May 22, 2009 and later published as WO 2009/143425 on Nov. 26, 2009 (Applicant—The Regents of the University of California // Inventors—Schmidt, et al.) (3 pages).
Akeson et al., "Microsecond Time-Scale Discrimination Among Polycytidylic Acid, Polyadenylic Acid, and Polyuridylic Acid as Homopolymers or as Segments Within Single RNA Molecules," *Biophys J* 1999, 77:3227-3233.
Albertero, et al., "The $\alpha$, $\alpha$-(1→1) Linkage of Trehalose is Key to Anhydrobiotic Preservation," *J. Am Chem Soc* 2007, 129(34):10567-10574.
Alexandridis, "Amphiphilic copolymers and their applications," *Curr Opin Colloid Interface Sci* 1996, 1(4):490-501.
Andersson, et al., "TRPM8 Activation by Menthol, Icilin, and Cold is Differentially Modulated by Intracellular pH," *J Neurosci* 2004, 24:5364-5369.
Anrather et al., "Supported Membrane Nanodevices," *J Nanosci Nanotech* 2004, 4(1/2):1-22.
Baaken, et al., "Nanopore-Based Single-Molecule Mass Spectrometry on a Lipid Membrane Microaaray," *ACS Nano* 2011, 5:8080-8088.
Baaken, et al., "Planar microelectrode-cavity array for high-resolution and parallel electrical recording of membrane ionic currents," *Lab Chip* 2008, 8:938-944.
Bainbridge et al., "Voltage gating is a fundamental feature of porin and toxin beta-barrel membrane channels," *FEBS Lett* 1998, 431(3):305-308.
Bautista et al., "The menthol receptor TRPM8 is the principal detector of environmental cold," *Nature* 2007, 448:204-208.
Bayley et al., "Droplet interface bilyaers," *Mol Biosyst* 2008, 4:1191-1208.

(56) References Cited

OTHER PUBLICATIONS

Bayley et al., "Stochastic sensors inspired by biology," *Nature* 2001, 413(6852):226-230.
Beddow et al., "Reconstitution of nicotinic acetylcholine receptors into gel-protected lipid membranes," *Anal Chem* 2004, 76(8):2261-2265.
Behrendt et al., "Characterization of the mouse cold-menthol receptor TRPM8 and vanilloid receptor type-1 VR1 using a fluorometric imaging plate reader (FLIPR) assay," *Br J Pharmacol* 2004, 141:737-745.
Blake et al., "Monitoring chemical reactions by using ion-channel-forming peptides," *Chembiochem* 2006, 7:433-435.
Blaustein et al., "Anthrax Toxin—Channel-Forming Activity of Protective Antigen in Planar Phospholipid-Bilayers," *Proc Natl Acad Sci USA* 1989, 86:2209-2213.
Braha et al., "Designed protein pores as components for biosensors," *Chemistry and Biology* 1997, 4:497-505.
Braha et al., "Simultaneous stochastic sensing of divalent metal ions," *Nature Biotechnology* 2000, 18:1005-1007.
Brauchi et al., "Clues to understanding cold sensation: Thermodynamics and electrophysiological analysis of the cold receptor TRPM8," *Proc Natl Acad Sci USA* 2004, 101:15494-15499.
Brohawn et al., "Crystal structure of the human K2P TRAAK, a lipid- and mechano-sensitive K+ ion channel," *Science* 2012, 335(6067):436-441.
Canal et al., "Correlation between mesh size and equilibrium degree of swelling of polymeric networks," *J Biomed Mater Res* 1989, 23(10):1183-93.
Capone et al., "Designing Nanosensors Based on Charged Derivatives of Gramicidin A," *J Am Chem Soc* 2007, 129:9737-9745.
Chachin et al., "Epinastine, a nonsedating histamine H1 receptor antagonist, has a negligible effect on HERG channel," *Eur J Pharmacol* 1999, 374(3):457-460.
Cheley et al., "Stochastic sensing of nanomolar inositol 1,4,5-trisphosphate with an engineered pore," *Chem Biol* 2002, 9:829-838.
Chen et al., "Position of aromatic residues in the S6 domain, not inactivation, dictates cisapride sensitivity of HERG and eag potassium channels," *Proc Natl Acad Sci* 2002, 99(19):12461-12466.
Cheng et al., "A high-throughput HERG potassium channel function assay: An old assay with a new look," *Drug Dev Indust Pharm* 2002, 28(2):177-191.
Chiu et al., "Validation of a [3H]astemizole binding assay in HEK293 cells expressing Herg K+ channels," *J Pharmacol Sci* 2004, 95(3):311-319.
Chuang et al., "The super-cooling agent icilin reveals a mechanism of coincidence detection by a temperature-sensitive TRP channel," *Neuron* 2004, 43:859-869.
Cohen, "Fusion of phospholipid vesicles with planar phospholipid bilayer membranes. II. Incorporation of a vesicular membrane marker into the planar membrane," *J Gen Physiol* 1980, 75:251-270.
Colburn et al., "Attenuated cold sensitivity in TRPM8 null mice," *Neuron* 2007, 54:379-386.
Comley, "Patchers verses screener: divergent opinion on high throughput electro-physiology," *Drug Discovery World* 2003, 47-57.
Costello et al., "Improved gel-protected bilayers," *Biosensors Bioelectronics* 1999, 14(3):265-271.
Diaz et al., "The [3H]dofetilide binding assay is a predictive screening tool for hERG blockade and proarrhythmia: Comparison of intact cell and membrane preparations and effects of altering [K+]," *J Pharmacol Toxicol Methods* 2004, 50(3):187-199.
Dragoni et al., "The Cold and Menthol Receptor TRPM8 Contains a Functionally Important Double Cysteine Motif," *J Biol Chem* 2006, 281:37353-37360.
Dunlop et al., "High-throughput electrophysiology: an emerging paradigm for ion-channel screening and physiology," *Nature Reviews Drug Discovery* 2008, 7:358-368.
Eccles, "Methanol and related cooling compounds," *J Pharm Pharmacol* 1994, 46:618-630.
El-Arabi et al., "Ion channel drug potency assay with an artificial bilayer chip," *Lab Chip* 2012, 12(13):2409-2413.
Falconer et al., "High-Throughput Screening for Ion Channel Modulators," *J Biomolec Screen* 2002, 7(5):460-465.
Favero et al., "Membrane supported lipid bilayer membranes array: preparation, stability and ion-channel insertion," *Analytica Chimica Acta* 2002, 460(1):23-34.
Fernández et al., "Voltage- and cold-dependent gating of single TRPM8 ion channels," *J Gen Physiol* 2011, 137:173-195.
Funakoshi et al., "Lipid bilayer formation by contacting monolayers in a microfluidic device for membrane protein analysis," *Anal Chem* 2006, 78:8169-8174.
Golowasch et al., "Allosteric effects of Mg2+ on the gating of Ca2+-activated K+ channels from mammalian skeletal muscle," *J Exp Biol* 1986, 124(1):5-13.
Gu et al., "Stochastic sensing of organic analytes by a pore-forming protein containing a molecular adapter," *Nature* 1999, 398:686-690.
Guan et al., "Stochastic sensing of TNT with a genetically engineered pore," *Chembiochem* 2005, 6:1875-1881.
Han et al., "Nanopore Arrays for Stable and Functional Free-Standing Lipid Bilayers," *Adv Mater* 2007, 19:4466-4470.
Hancox et al., "The hERG potassium channel and hERG screening for drug-induced torsades de pointes," *Pharmacol Therapeut* 2008, 119(2):118-132.
Hanke & Schlue, "Planar Lipid Bilayers: Methods and Applications," *Academic Press*, London; New York 1993.
Hartgerink et al., "Self-Assembly and Mineralization of Peptide-Amphiphile Nanofibers," *Science* 2001, 294(5547):1684-1688.
Hartgerink et al., "Supramolecular Chemistry and Self-assembly Special Feature: Peptide-amphiphile nanofibers: A versatile scaffold for the preparation of self-assembling materials," *Proc Natl Acad Sci* 2002, 99(8):5133-5138.
Heron et al., "Direct detection of membrane channels from gels using water-in-oil droplet bilayers," *J Am Chem Soc* 2007, 129(51):16042-16047.
Hertzberg & Pope, "High-throughput screening: new technology for the 21st century," *Curr Opin Chem Biol* 2000, 4:445-451.
Hirano et al., "Lipid Bilayers at Gel/Gel Interface for Ion Channel Recordings," *J Surf Sci Nanotech* 2008, 6:130-133.
Holden et al., "Functional bionetworks from nanoliter water droplets," *J Am Chem Soc* 2007, 129:8650-8655.
Hromada et al., "Single molecule measurements within individual membrane-bound ion channels using a polymer-based bilayer lipid membrane chip," *Lab Chip* 2008, 8:602-608.
Hu et al., "2-Aminoethoxydiphenyl borate is a common activator of TRPV1, TRPV2, and TRPV3," *J Biol Chem* 2004, 279:35741-35748.
Hwang et al., "Asymmetric droplet interface bilayers," *J Am Chem Soc* 2008, 130:5878-5879.
Ide et al., "Lipid Bilayers at the Gel Interface for Single Ion Channel Recordings," *Anal Chem* 2008, 80(20):7792-7795.
Ide et al., "An Artificial Lipid Bilayer Formed on an Agarose-Coated Glass for Simultaneous Electrical and Optical Measurement of Single Ion Channels," *Biochem Biophys Res Commun* 1999, 265:595-599.
Ide et al., "Simultaneous Optical and Electrical Recording of a Single Ion-Channel," *Japanese J Physiol* 2002, 52:429-434.
Ionescu-Zanetti et al., "Mammalian electrophysiology on a microfluidic platform," *Proc Natl Acad Sci USA* 2005, 102: 9112-9117.
Jacobson et al., "Microchip structures for submillisecond electrophoresism" *Analytical Chemistry* (1998) 70, 3476.
Jeon et al., "Long term storable and shippable liquid bilayer membrane platform," *Lab Chip* 2008, 8:1742-1744.
Jeon et al., "Black lipid membranes stabilized through substrate conjugation to a hydrogel," *Biointerphases* 2008, 3:96-100.
Jeon et al., "Hydrogel-Encapsulated Lipid Membranes," *J Am Chem Soc* 2006, 128(1):42-43.
Joanicot et al., "Droplet control for microfluidics," *Science* 2005, 309(5726):887-888.
Kang et al., "A Storable Encapsulated Bilayer Chip Containing a Single Protein Nanopore," *J Am Chem Soc* 2007, 129(15):4701-4705.

(56) References Cited

OTHER PUBLICATIONS

Kasianowicz et al., "Characterization of individual polynucleotide molecules using a membrane channel," *Proc Natl Acad Sci USA* 1996, 93, 13770-13773.
Kazakov et al., "UV-induced gelation on nanometer scale using liposome reactor," *Macromolecules* 2002, 35(5):1911-1920.
Keating et al., "Molecular and Cellular Mechanisms of Cardiac Arrhythmias," *Cell* 2001, 104:569-580.
Kedei et al., "Analysis of the native quaternary structure of vanilloid receptor 1," *J Biol Chem* 2001, 276:28613-28619.
Kiehn et al., "Cellular and Molecular Cardiology: Molecular Physiology and Pharmacology of HERG: Single-Channel Currents and Block by Dofetilide," *Circulation* 1996, 94(10):2572-2579.
Kloxin et al., "Photodegradable Hydrogels for Dynamic Tuning of Physical and Chemical Properties," *Science* 2009, 324(5923):59-63.
Knoll et al., "Functional tethered lipid bilayers," *Rev Mol Biotech* 2000, 74(3):137-158.
Krishna et al. "Tethered Bilayer Membranes Containing Ionic Reservoirs: Selectivity and Conductance," *Langmuir* 2003, 19:2294-2305.
Kuhner et al., "Lipid mono- and bilayer supported on polymer films: composite polymer-lipid films on solid substrates," *Biophys J* 1994, 67(1):217-226.
Lashinger et al., "AMTB, a TRPM8 channel blocker: evidence in rats for activity in overactive bladder and painful bladder syndrome," *Am J Physiol Renal Physiol* 2008, 295:803-810.
Le Pioufle et al., "Lipid bilayer microarray for parallel recording of transmembrane ion currents," *Anal Chem* 2008, 80:328-332.
Lee et al., "Photoreversible viscosity changes and gelation in mixtures of hydrophobically modified polyelectrolytes and photosensitive surfactants," Macromolecules 2004, 37:5397-5405.
Lee et al., "Solvent compatibility of poly(dimethylsiloxane)-based microfluidic devices," *Anal Chem* 2003, 75(23):6544-6554.
Leptihn et al., "In Vitro Reconstitution of Eukaryotic Ion Channels using Droplet Interface Bilayers," J Am Chem Soc 2011, 133:9370-9375.
Liu & Qin, "Functional control of cold- and menthol-sensitive TRPM8 ion channels by phosphatidylinositol 4,5-bisphosphate," *J Neurosci* 2005, 25:1674-1681.
Long et al., "Atomic structure of a voltage-dependent K+ channel in a lipid membrane-like environment," *Nature* 2007, 450:376-382.
Lu et al., "Biophysical aspects of agar-gel supported bilayer lipid membranes: a new method for forming and studying planar bilayer lipid membranes," *Bioelectrochem Bioenergetics* 1996, 39:285-289.
Lustig et al., "Solute Diffusion in Swollen Membranes .9. Scaling Laws for Solute Diffusion in Gels," *J Appl Polymer Sci* 1988, 36(4):735-747.
Malmstadt et al., "Automated formation of lipid-bilayer membranes in a microfluidic device," *Nano Letters* 2006, 6:1961-1965.
Malmstadt et al., "Long-Lived Planar Lipid Bilayer Membranes Anchored to an In Situ Polymerized Hydrogel," *Adv Mater* 2008, 20(1):84-89.
Malmstadt et al., "New approaches to lipid bilayer fabrication: microfluidic solvent extraction and hydrogel encapsulation," Adv Sci Technol 2006, 53:22-31.
Martens et al., "Tailoring the degradation of hydrogels formed from multivinyl poly(ethylene glycol) and poly(vinyl alcohol)macromers for cartilage tissue engineering," *Biomacromolecules* 2003, 4:283-292.
Matthews et al., "Design and fabrication of a micromachined planar patch-clamp substrate with integrated microfluidics for single-cell measurements," *J MEMS* 2006, 15: 214-222.
Mayer et al., "Microfabricated teflon membranes for low-noise recordings of ion channels in planar lipid bilayers," *Biophys J* 2003, 85:2684-2695.
Mayer et al., "Using ion channel-forming peptides to quantify protein-ligand interactions," J Am Chem Soc 2008, 130:1453-1465.
Maynard et al., "Thermoresponsive biohybrid materials synthesized by ATRP," *J Mater Chem* 2007, 17:4015-4017.

McDonald et al., "Poly(dimethylsiloxane) as a material for fabricating microfluidic devices," *Acct Chem Res* 2002, 35(7):491-499.
McKemy et al., "Identification of a cold receptor reveals a general role for TRP channels in thermosensation," *Nature* 2002, 416:52-58.
Meller et al., "Rapid nanopore discrimination between single polynucleotide molecules," *Proc Natl Acad Sci* 2000, 97:1079-1084.
Miller, "Ion Channel Reconstitution." Plenum Press, New York 1986.
Molokanova et al., "Bright future of optical assays for ion channel drug discovery," *Drug Discovery Today* 2008, 13:14-22.
Montal et al., "Formation of Bimolecular Membranes from Lipid Monolayers and a Study of Their Electrical Properties," *Proc Natl Acad Sci* 1972, 69(12):3561-3566.
Moscho et al., "Rapid preparation of giant unilamellar vesicles," Proc Natl Acad Sci 1996, 93:11443-11447.
Mueller et al., "Reconstitution of cell membrane structure in vitro and its transformation into an excitable system," *Nature* 1962, 194:979-980.
Nakane et al., "Nanopore sensors for nucleic acid analysis," J Phys Condensed Matter 2003, 15(32):R1365-R1393.
Naumowicz et al., "Impedance analysis of phosphatidylcholine membranes modified with gramicidin D," *Bioelectrochem* 2003, 61:21-27.
Nilius, "TRP channels in disease," Biochimica Et Biophysica Acta—Molecular Basis of Disease 2007, 1772:805-812.
Ottova & Tien, "Self-assembled bilayer lipid membranes: from mimicking biomembranes to practical applications," Bioelectrochem Bioenergetics 1997, 42:141-152.
Peier et al., "A TRP Channel that Senses Cold Stimuli and Menthol," Cell 2002, 108:705-715.
Perez et al., "Reconstitution of Expressed K-Ca Channels from Xenopus-Oocytes to Lipid Bilayers," Biophys J 1994, 66:1022-1027.
Portonovo & Schmidt, "Masking apertures enabling automation and solution exchange in sessile droplet lipid bilayers," *Biomed Microdevices* 2011, 14:187-191.
Poulos et al., "Automatable production of shippable bilayer chips by pin tool deposition for an ion channel measurement platform," *Biotechnol J* 2010, 5:511-514.
Poulos et al., "Automatable lipid bilayer formation and ion channel measurement using sessile droplets," *J Phys: Condens Matter* 2010, 22:454105.
Poulos et al., "Automatable lipid bilayer formation for ion channel studies," SPIE Proceedings 2008, 7035 (6 pages).
Poulos et al., "Electrowetting on dielectric-based microfluidics for integrated lipid bilayer formation and measurement," *Appl Phys Lett* 2009, 95 (3 pages).
Poulos et al., "Ion channel and toxin measurement using a high throughput lipid membrane platform," *Biosens Bioelectron* 2009, 24:1806-1810.
Purnell et al., "Nucleotide Identification and Orientation Discrimination of DNA Homopolymers Immobilized in a Protein Nanopore," NanoLetters 2008, 8(9):3029-3034.
Rehak et al., "Examination of bilayer lipid membranes for 'pin-hole' character," *The Analyst* 2004, 129:1014-1025.
Rohács et al., "PI(4,5)P2 regulates the activation and desensitization of TRPM8 channels through the TRP domain," *Nat Neurosci* 2005, 8:626-634.
Rosenbaum et al., "Subunit modification and association in VR1 ion channels," *BMC Neurosci* 2002, 3:4-13.
Sakmann & Neher (eds.), "Single-channel recording," Plenum Press, New York 1995.
Sakmann & Neher, "Patch clamp techniques for studying ionic channels in excitable membranes," Ann Rev Physiol 1984, 46:455-472.
Sandison et al., "Air-exposure technique for the formation of artificial lipid bilayers in microsystems," *Langmuir* 2007, 23:8277-8284.
Sandison et al., "Micromachined glass apertures for artificial lipid bilayer formation in a microfluidic system," *J Micromech Microeng* 2007, 17:S189-S196.
Sandison et al., "Rapid fabrication of polymer microfluidic systems for the production of artificial lipid bilayers," *J. Micromech Microeng* 2005, 15: S139-S144.
Schein et al., "Reconstitution in planar lipid bilayers of a voltage-dependent anion-selective channel obtained from *Paramecium* mitochondria," *J Membrane Biol* 1976, 30(1):99-120.

(56) References Cited

OTHER PUBLICATIONS

Schindler & Quast, "Functional acetylcholine receptor from *Torpedo marmorata* in planar membranes," *Proc Natl Acad Sci* 1980, 77(5):3052-3056.
Schindler & Rosenbusch, "Matrix Protein from *Escherichia coli* Outer Membranes Forms Voltage-Controlled Channels in Lipid Bilayers," Proc Natl Acad Sci 1978, 75(8):3751-3755.
Schindler, "Formation of Planar Bilayers from Artificial or Native Membrane-Vesicles," FEBS Lett 1980, 122:77-79.
Schmalhofer et al., "A Pharmacologically Validated, High-Capacity, Functional Thallium Flux Assay for the Human Ether-à-go-go Related Gene Potassium Channel," Assay Drug Dev Technol 2010, 8(6):714-726.
Shim et al., "Stochastic Sensing on a Modular Chip Containing a Single Ion Channel," *Anal Chem* 2007, 79(6):2207-2213.
Sia et al., "Microfluidic devices fabricated in poly(dimethylsiloxane) for biological studies," *Electrophoresis* 2003, 24(21):3563-3576.
Sinner et al., "Functional tethered membranes," Curr Opinion Chem Biol 2001, 5(6):705-711.
Song et al., "Millisecond kinetics on a microfluidic chip using nanoliters of reagents," *J Am Chem Soc* 2003, 125(47):14613-14619.
Song et al., "Structure of staphylococcal alpha-hemolysin, a heptameric transmembrane pore," *Science* 1996, 274(5294):1859-66.
Suarezisla et al., "Single-Channel Recordings from Purified Acetylcholine-Receptors Reconstituted in Bilayers Formed at the Tip of Patch Pipets," Biochemistry 1983, 22:2319-2323.
Suzuki et al., "Electrophysiological recordings of single ion channels in planar lipid bilayers using a polymethyl methacrylate microfluidic chip," Biosens Bioelectron 2007, 22:1111-1115.
Suzuki et al., "Highly reproducible method of planar lipid bilayer reconstitution in polymethyl methacrylate microfluidic chip," *Langmuir* 2006, 22: 1937-1942.
Suzuki et al., "Planar lipid bilayer reconstitution with a microfluidic system," Lab Chip 2004, 4:502-505.
Syeda et al., "Screening Blockers Against a Potassium Channel with a Droplet Interface Bilayer Array," J Am Chem Soc 2008, 130:15543-15548.
Takagi et al., "A new method for the formation of bilayer membranes in aqueous solutions," Ann Rep Biol Fac Sci Osaka 1965, 13:107-110.
Tao & MacKinnon, "Functional analysis of Kv1.2 and paddle chimera Kv channels in planar lipid bilayers," *J Mol Biol* 2008, 382:24-33.
Terrettaz et al., "Highly Electrically Insulating Tethered Lipid Bilayers for Probing the Function of Ion Channel Proteins," *Langmuir* 2003, 19:5567-5569.
Thapliyal et al., "Automated lipid bilayer and ion channel measurement platform," Biosens Bioelectron 2011, 26:2651-2654.
Thorsen et al. "Microfluidic large-scale integration," *Science* (2002) 298, 580.
Thorsen et al., "Dynamic pattern formation in a vesicle-generating microfluidic device," *Phys Rev Lett* 2001, 86(18):4163-4166.
Titus et al., "A new homogeneous high-throughput screening assay for profiling compound activity on the human ether-a-go-go-related gene channel," *Analyt Biochem* 2009, 394(1):30-38.
Trenor et al., "Photoreversible Chain Extension of Poly(ethylene glycol)," Macromolec Chem Phys 2004, 205(6):715-723.
Tsavaler et al., "Trp-p8, a novel prostate-specific gene, is up-regulated in prostate cancer and other malignancies and shares high homology with transient receptor potential calcium channel proteins," Cancer Res 2001, 61:3760-3769.
Tsofina et al., "Production of Bimolecular Protein-Lipid Membranes in Aqueous Solution," Nature 1966, 212:681-683.
Unger et al., "Monolithic microfabricated valves and pumps by multilayer soft lithography," *Science* 2000, 288(5463), 113-116.
Vodyanoy et al., "Alamethicin-Induced Current-Voltage Curve Asymmetry in Lipid Bilayers," *Biophys J* 1983, 42:71-82.

Wang et al., "Development of a novel solid-phase extraction element for thermal desorption gas chromatography analysis," *J Chrom A* 2004, 1035(2):277-279.
Weigl et al., "Lab-on-a-chip for drug development," Adv Drug Delivery 2003, 55:349-377.
White, "The physical nature of planar bilayer membranes," in *Ion Channel Reconstitution*, Plenum Press, New York 1986, pp. 3-35.
Wonderlin et al., "Optimizing Planar Lipid Bilayer Single-Channel Recordings for High-Resolution with Rapid Voltage Steps," *Biophys J* 1990, 58:289-297.
Wong et al., "Single molecule measurements of channel proteins incorporated into biomimetic polymer membranes," Nanotechnology 2006, 17:3710-3717.
Wulff et al., "Voltage-gated potassium channels as therapeutic targets," Nat Rev Drug Discov 2009, 8(12):982-1001.
Yuan et al., "Bilayer Thickness Modulates the Conductance of the BK Channel in Model Membranes," Biophys J 2004, 86(6):3620-3633.
Zagnoni et al., "Bilayer lipid membranes from falling droplets," Anal Bioanal Chem 2009, 393:1601-1605.
Zagnoni et al., "Microfluidic array platform for simultaneous lipid bilayer membrane formation," Biosens Bioelectron 2009, 24:1235-1240.
Zakharian et al., "Gating of Transient Receptor Potential Melastatin 8 (TRPM8) Channels Activated by Cold and Chemical Agonists in Planar Lipid Bilayers," *J Neurosci* 2010, 30:12526-12534.
Zakharian et al., "Inorganic polyphosphate modulates TRPM8 channels," *PLoS One* 2009, 4 (12 pages).
Zhang & Barritt, "TRPM8 in prostate cancer cells: a potential diagnostic and prognostic marker with a secretory function?" *Endocr Relat Cancer* 2006, 13:27-38.
Zheng et al., "Screening of protein crystallization conditions on a microfluidic chip using nanoliter-size droplets," *J Am Chem Soc* 2003, 125(37):11170-11171.
Zholos, "Pharmacology of transient receptor potential melastatin channels in the vasculature," Brit J Pharmacol 2010, 159:1559-1571.
Zhou et al., "Properties of HERG channels stably expressed in HEK 293 cells studied at physiological temperature," *Biophys J* 1998, 74(1):230-241.
Zou et al., "Single HERG delayed rectifier K+ channels expressed in Xenopus oocytes," *Am J Physiol-Heart Circ Physiol* 1997, 272(3):H1309-H1314.
Preliminary Amendment filed Apr. 11, 2008 for U.S. Appl. No. 12/083,410, filed Oct. 13, 2006 and later granted as US Patent No. 8,038,885 on Oct. 18, 2011 (Inventors—Jacob J. Schmidt et al.) (10 pages).
Requirement for Restriction/Election issued Oct. 4, 2010 for U.S. Appl. No. 12/083,410, filed Oct. 13, 2006 and later granted as U.S. Patent No. 8,038,885 on Oct. 18, 2011 (Inventors—Jacob J. Schmidt et al.) (7 pages).
Response to Election/Restriction filed Nov. 10, 2010 for U.S. Appl. No. 12/083,410, filed Oct. 13, 2006 and later granted as U.S. Patent No. 8,038,885 on Oct. 18, 2011 (Inventors—Jacob J. Schmidt et al.) (9 pages).
Non-Final Rejection issued Nov. 18, 2010 for U.S. Appl. No. 12/083,410, filed Oct. 13, 2006 and later granted as U.S. Patent No. 8,038,885 on Oct. 18, 2011 (Inventors—Jacob J. Schmidt et al.) (7 pages).
Response to Non-Final Rejection filed May 6, 2011 for U.S. Appl. No. 12/083,410, filed Oct. 13, 2006 and later granted as U.S. Patent No. 8,038,885 on Oct. 18, 2011 (Inventors—Jacob J. Schmidt et al.) (13 pages).
Notice of Allowance issued Jun. 16, 2011 for U.S. Appl. No. 12/083,410, filed Oct. 13, 2006 and later granted as U.S. Patent No. 8,038,885 on Oct. 18, 2011 (Inventors—Jacob J. Schmidt et al.) (13 pages).
Non-Final Rejection issued Nov. 1, 2013 for U.S. Appl. No. 13/269,433, filed Oct. 7, 2011 (Inventors—Jacob J. Schmidt et al.) (8 pages).
Applicant Initiated Interview Summary (PTOL-413) issued on Nov. 20, 2013 for U.S. Appl. No. 13/269,433, filed Oct. 7, 2011 (Inventors—Jacob J. Schmidt et al.) (3 pages).

(56) References Cited

OTHER PUBLICATIONS

Preliminary Amendment filed Nov. 19, 2010 for U.S. Appl. No. 12/993,713, filed Feb. 1, 2011 (Inventors—Jacob J. Schmidt et al.) (8 pages).
Non-Final Rejection issued Jul. 8, 2013 for U.S. Appl. No. 12/993,713, filed Feb. 1, 2011 (Inventors—Jacob J. Schmidt et al.) (12 pages).
Applicant Initiated Interview Summary (PTOL-413) issued Sep. 26, 2013 for U.S. Appl. No. 12/993,713, filed Feb. 1, 2011 (Inventors—Jacob J. Schmidt et al.) (3 pages).
Amendment and Reponse to Office action filed Oct. 15, 2013 for U.S. Appl. No. 12/993,713, filed Feb. 1, 2011 (Inventors—Jacob J. Schmidt et al.) (10 pages).
Applicant Initiated Interview Summary (PTOL-413) issued Oct. 15, 2013 for U.S. Appl. No. 12/993,713, filed Feb. 1, 2011 (Inventors—Jacob J. Schmidt et al.) (3 pages).
Supplemental Amendment and Response to Office Action filed Nov. 8, 2013 for U.S. Appl. No. 12/993,713, filed Feb. 1, 2011 (Inventors—Jacob J. Schmidt et al.) (7 pages).
Notice of Allowance issued Mar. 3, 2014 for U.S. Appl. No. 12/993,713, filed Feb. 1, 2011 (Inventors—Jacob J. Schmidt et al.) (8 pages).
International Search Report issued May 3, 2007 by the International Searching Authority for Application PCT/US2006/040200 filed Oct. 13, 2006, which published as WO 2007/047498 on Apr. 26, 2007 (Applicant—The Regents of the University of California // Inventors—Jacob J. Schmidt, et al.) (2 pages).
Written Opinion issued May 3, 2007 by the International Searching Authority for Application PCT/US2006/040200 filed Oct. 13, 2006, which published as WO 2007/047498 on Apr. 26, 2007 (Applicant—The Regents of the University of California // Inventors—Jacob J. Schmidt, et al.) (5 pages).
International Preliminary Report on Patentability issued Apr. 16, 2008 by the International Searching Authority for Application PCT/US2006/040200 filed Oct. 13, 2006, which published as WO 2007/047498 on Apr. 26, 2007 (Applicant—The Regents of the University of California // Inventors—Jacob J. Schmidt, et al.) (6 pages).
International Search Report issued Mar. 21, 2011 by the International Searching Authority for Application PCT/US2011/020284 filed Jan. 5, 2011, which published as WO 2011/085047 on Jul. 14, 2011 (Applicant—The Regents of the University of California // Inventors—Jason L. Poulos, et al.) (2 pages).
Written Opinion issued Mar. 21, 2011 by the International Searching Authority for Application PCT/US2011/020284 filed Jan. 5, 2011, which published as WO 2011/085047 on Jul. 14, 2011 (Applicant—The Regents of the University of California // Inventors—Jason L. Poulos, et al.) (8 pages).
International Preliminary Report on Patentability issued Jul. 10, 2012 by the International Bureau for Application PCT/US2011/020284 filed Jan. 5, 2011, which published as WO 2011/085047 on Jul. 14, 2011 (Applicant—The Regents of the University of California // Inventors—Jason L. Poulos, et al.) (9 pages).
International Search Report issued Oct. 26, 2009 by the International Searching Authority for Application PCT/US2009/044979 filed May 22, 2009, which published as WO 2009/143425 on Nov. 26, 2009 (Applicant—The Regents of the University of California // Inventors—Jacob J. Schmidt, et al.) (3 pages).
Written Opinion issued Oct. 26, 2009 by the International Searching Authority for Application PCT/US2009/044979 filed May 22, 2009, which published as WO 2009/143425 on Nov. 26, 2009 (Applicant—The Regents of the University of California // Inventors—Jacob J. Schmidt, et al.) (4 pages).
International Preliminary Report on Patentability issued Nov. 23, 2010 by the International Bureau for Application PCT/US2009/044979 filed May 22, 2009, which published as WO 2009/143425 on Nov. 26, 2009 (Applicant—The Regents of the University of California // Inventors—Jacob J. Schmidt, et al.) (5 pages).
Extended European Search Report issued on Apr. 23, 2013 for European Application No. 09751653.8, which is anational phase of PCT/US2009/044979, filed May 22, 2009 and later published as WO 2009/143425 on Nov. 26, 2009 (Applicant—The Regents of the University of California // Inventors—Jacob J. Schmidt, et al.) (8 pages).

DROPLET BILAYER FORMATION USING THROUGHPUT LIQUID HANDLING TECHNIQUES

CROSS-REFERENCE TO RELATED APPLICATIONS

This application claims the benefit of U.S. Application No. 61/292,361 filed Jan. 5, 2010, which is hereby incorporated herein by reference in its entirety.

BACKGROUND

Planar lipid bilayer platforms are widely used in the study of ion channels. As opposed to techniques involving the isolation of ion channels over patches of live cells, planar lipid bilayer platforms are engineered systems that allow for greater levels of control over the membrane environment surrounding reconstituted ion channels. They also allow for superior control over the aqueous compartments adjacent to the membrane.

In spite of these advantages, artificial lipid bilayers are characterized by shortcomings of fragility and short lifetime and the necessity for a human operator to form them at the time and place of use. This is typically a very low throughput one-off process, which has significantly limited their technological prospects. Yet, if these shortcomings of traditional bilayer platforms can be reduced, specifically the expertise required to perform experimentation and increased experimental throughput, artificial planar bilayers can function as a useful tool in the study of ion channels.

Using the contacting monolayer (CM) method (Poulos, J, "Ion channel and toxin measurement using a high throughput lipid membrane platform," *Biosensors & Bioelectronics*, 24:1806-1810, 2009), which is incorporated by reference herein in its entirety, planar lipid bilayers can be formed. The CM method involves the mechanical contacting of two individual lipid monolayers, thereby forming a bilayer.

When an aqueous droplet is placed in an organic solvent and either liquid contains dissolved lipid molecules, the lipids will self-assemble at the aqueous/organic interface, forming a monolayer. Production of a lipid bilayer is possible if two such monolayers are mechanically brought into contact. Recently, this method was used in microfluidic systems for bilayer formation. Bilayers were formed by extracting the organic solvent through the device, or by contacting the aqueous phases by applying pressure. In addition to this, a version of this method created networks of bilayers by combining them with a micromanipulator. The CM method was also adapted to a vertical orientation, where a droplet was placed on a hydrogel support and used to track single molecules optically. These methods used manual manipulation of the phases to create bilayers.

Electrical measurement of ion channels involves electrical access to each side of the bilayer in which the ion channels are inserted. For artificially formed bilayers, this involves placing an electrode in the aqueous solutions on each side of the bilayer. However, placement of the electrode can perturb one or both of the aqueous solutions sufficiently to disturb or destroy the bilayer. The bilayer can be reformed by manipulating the position of the electrode, but this compromises the high throughput of the bilayer formation process.

In the work of Ide et al. (*Anal Chem*, 2008. 80(20): p. 7792-5), which is incorporated by reference herein in its entirety, one half of the bilayer-forming aqueous solution was made from a hydrogel. An electrode was insertable into the hydrogel without compromising the bilayer. Although this may appear to address the concerns associated with the compatibility of electrical measurement with high throughput bilayer formation, if there is an analyte or protein solution in the hydrogel, the hydrogel should be exchanged for a subsequent measurement. This would necessitate the prior synthesis of a large amount of hydrogel-filled capillaries which would need to be exchanged for high throughput bilayer formation.

Therefore, there remains a need for methods and compositions that overcome these deficiencies and can increase the degree of throughput in lipid bilayer formation and measurement.

SUMMARY

In accordance with the purposes of the disclosed materials, compounds, compositions, articles, devices, and methods, as embodied and broadly described herein, the disclosed subject matter, in one aspect, relates to methods and/or materials for preparing and using bilayers as well as bilayers prepared by the disclosed methods. In a particular aspect, disclosed are methods for the high throughput preparation of bilayers as well as enabling the high throughput measurement of the produced bilayers.

In accordance with the purpose(s) of the invention, as embodied and broadly described herein, the invention, in one aspect, relates to devices for preparing, measuring, and using lipid bilayers, lipid bilayers produced therefrom, and methods for producing and measuring same.

Disclosed are methods for forming a lipid bilayer, comprising the steps of a) providing a droplet electrode with a tip having at least a droplet of aqueous solution, b) providing a well comprising an upper organic phase, a lower aqueous phase, and a well electrode extending into the lower aqueous phase, wherein at least one of the aqueous solution, the lower aqueous phase, and the upper organic phase comprise lipids, and wherein the droplet electrode and the well electrode are in electrical communication, and c) inserting the droplet electrode into the well so that a lipid bilayer forms between the lower aqueous phase of the well and the aqueous solution of the droplet electrode tip.

Also disclosed are methods for forming a lipid bilayer wherein the at least a droplet of aqueous solution is a sessile droplet positioned at the tip of the droplet electrode.

Also disclosed are methods for measuring current through a bilayer, comprising a) providing a pin tool, wherein the tool comprises an electrode and contains an aqueous solution and lipid vesicles, b) providing a well, wherein the well comprises a lower aqueous phase and an upper organic phase, wherein the lower aqueous phase comprises an electrode and also comprises lipid vesicles, c) inserting the pin tool into the well so that a bilayer forms between the lower aqueous phase of the well and the aqueous solution of the pin tool; and d) measuring the current through the bilayer.

Also disclosed are high-throughput lipid bilayer production devices comprising a plurality of wells, each well having a well electrode positioned within; and a droplet electrode in electrical communication with each well electrode and positioned for insertion into any of the plurality of wells, the electrode having a tip capable of extracting a droplet of liquid, or an internal reservoir capable of extruding a droplet of liquid.

Also disclosed are electrode assemblies for use in high-throughput lipid bilayer production, the electrode assembly comprising an electrode carriage and a means for positioning the carriage, a droplet electrode mounted on the carriage and having a tip capable of extracting a droplet of liquid or an internal reservoir capable of extruding a droplet of liquid, and a well electrode in electrical communication with the droplet electrode and mounted on the carriage.

Also disclosed are well arrays for use in high-throughput lipid bilayer production, the well array comprising a plurality of wells, each well comprising an organic phase chamber, an aqueous phase chamber spaced apart from, but connected to, the organic phase chamber, and optionally, a membrane mask at the connection between the aqueous phase chamber and the organic phase chamber.

Also disclosed are the products of the disclosed methods.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1:
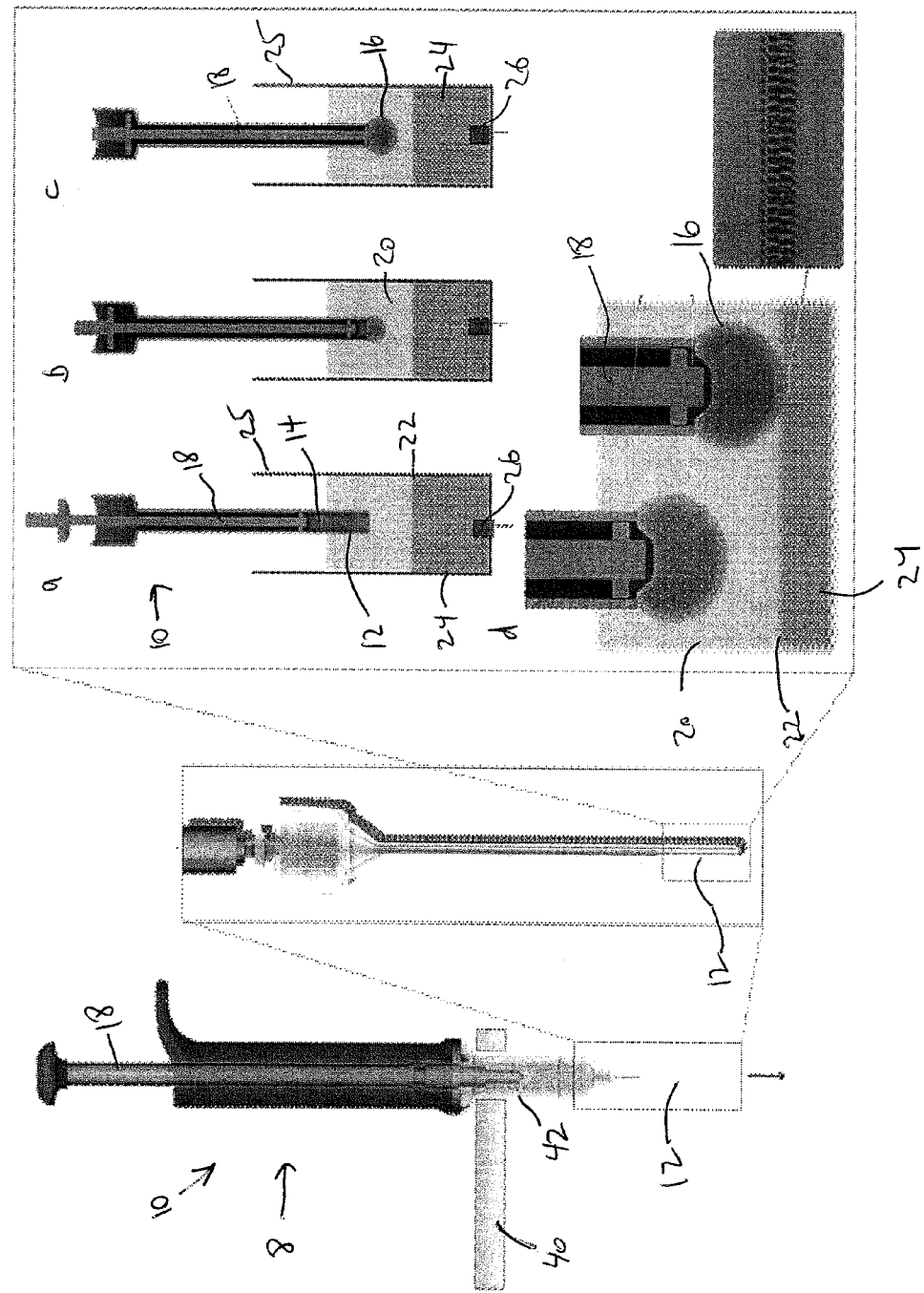
FIG. 1 is a series of views of methods and devices for forming a lipid bilayer, according to one aspect, showing the use of a positive displacement system.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

Although any methods and materials similar or equivalent to those described herein can be used in the practice or testing of the present invention, example methods and materials are now described.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a bilayer," "a tool," or "a step"

includes mixtures of two or more such functional compositions, tools, steps, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or can not occur, and that the description includes instances where said event or circumstance occurs and instances where it does not.

As used herein, the term "electrode" refers to an electrical conductor through which electric current is passed. Examples include wires, rods, ionic liquids, and the like.

As used herein, the term "aqueous phase" refers to a solution comprising at least one of pure water, salts and an electrolyte solution. The aqueous phase may also comprise at least one of lipid vesicles, liposomes made from DPhPC, and the like.

As used herein, the term "organic phase" refers to an organic solvent or oil. This phase may or may not contain lipids. Examples include decane, squalene, hexane, hexadecane, pentane, n-decane and the like.

As used herein, the term "lipids" refers to naturally occurring amphiphilic molecules which include fats, fatty acids, waxes, and sterols among others, used as structural components of cell membranes.

As used herein, the term "lipid bilayer" refers to a membrane formed of two monolayers of lipid molecules that form a barrier around cells and cellular organelles.

As used herein, the term "sessile droplet" refers to a hanging droplet, such as a droplet of an aqueous solution hanging from a droplet electrode.

As used herein, the term "membrane mask" refers to a mask than can form a barrier between the organic phase and a lower aqueous phase. Example mask materials include Teflon, Delrin, polyethylene, and most non-electrically conductive materials.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result. It is understood that the disclosed compositions, mixtures, and devices can be employed in connection with the disclosed methods and uses.

B. Formation of lipid layers

In one aspect, the invention relates to a method for forming a lipid bilayer. In a further aspect, the invention relates to methods of forming a lipid bilayer by joining lipid monolayers that self-assemble at the interface of aqueous and organic phases using sessile aqueous droplets in contact with a droplet electrode.

In one aspect, the method for forming a lipid bilayer comprises the steps of providing a droplet electrode with a tip having at least a sessile droplet of aqueous solution, and providing a well. In a further aspect, the well comprises an upper organic phase, a lower aqueous phase, and a well electrode extending into the lower aqueous phase. In this aspect, at least one of the aqueous solution, the lower aqueous phase, and the upper organic phase comprise lipids. Also in this aspect, the well electrode and the droplet electrode can be electrically coupled by, for example and without limitation, electrically coupling the electrodes to an amplifier. In a further aspect, the method for forming a lipid bilayer further comprises inserting the droplet electrode into the well so that a lipid bilayer forms between the lower aqueous phase of the well and the aqueous solution of the droplet electrode tip. In this aspect, the lipid bilayer is formed by joining the lipid monolayers formed on the surface of the lower aqueous phase of the well and the aqueous solution of the droplet electrode tip.

In one aspect, the inserting step of the method for forming a lipid bilayer comprises moving the droplet electrode and the sessile droplet of aqueous solution into the well, through the upper organic phase, and into contact with the lower aqueous phase, thereby forming a lipid bilayer at the location of contact between the droplet and the lower aqueous phase.

In one aspect, the droplet electrode tip can be capable of extracting a droplet of liquid. In another aspect, the droplet electrode tip can be capable of producing, presenting, and/or manipulating a droplet of liquid. For example, the at least a sessile droplet of aqueous solution can be a sessile droplet attached to and/or hanging from the droplet electrode. In a further aspect, the droplet electrode comprises a silver/silver chloride electrode (Ag/AgCl). In this aspect, the droplet electrode can comprise a silver electrode with a portion of its surface being chloridized. The Ag/AgCl coating can render the electrode conductive to ionic currents in electrolytes. In one aspect, the well electrode can comprise an Ag/AgCl wire.

In one aspect, the aqueous solution comprises a solution having at least one of lipid vesicles, liposomes made from DPhPC, and the like. In another aspect, the upper organic phase can comprise lipids and/or a lipid-containing organic solvent, such as decane, hexadecane, and the like.

1. Lipid Bilayer Formation Using a Positive Displacement Pipette

In one aspect, the droplet electrode has an internal reservoir capable of extruding a droplet of liquid. In a further aspect, the droplet of aqueous solution at the droplet electrode tip can be formed by extrusion from an internal reservoir.

For example, the droplet electrode 8 can be a positive displacement pipette 10, as illustrated in FIG. 1. The tip 12 of the pipette can be placed into a pool of a solution and a droplet of liquid can be extracted from the pool. An internal reservoir 14 of the pipette can store the extracted liquid, until a desired time at which a droplet 16 of the solution can be extruded from the tip of the pipette.

In one aspect, the pipette 10 can comprise a piston 18 configured to selectively draw solution through the tip 12 into the reservoir 14 or extrude solution from the reservoir through the tip. In another aspect, the piston can be an electrically conductive piston. In still another aspect, on an end of the piston, Ag/AgCl can be deposited.

In use, a droplet 16 can be formed on the tip of the droplet electrode by, for example, inserting a tip 12 of the pipette 10 into a sample well having an aqueous solution therein (not illustrated). Alternatively, a droplet can be formed on the tip of the droplet electrode by, for example, extracting a droplet of aqueous solution from the lower aqueous phase 24 before the upper organic phase 20 is positioned in the well 25. The aqueous solution can be withdrawn into the reservoir 14 of the pipette 10. In one aspect, the tip 12 of the pipette can be inserted into the upper organic phase 20 of the well, as illustrated in FIG. 1a. The piston can be lowered, incompletely expelling the aqueous solution through the pipette tip (FIGS. 1b and 1c). By this action, a droplet 16 of the aqueous solution, which can contain lipid vesicles, hangs extended from the pipette tip 12, but remains in contact with the conductive piston 18. A lipid monolayer will form at the droplet/organic phase interface. The pipette tip can then be lowered until the droplet makes contact with a lower interface 22 occurring between the upper organic phase 20 and the lower aqueous phase 24, which can contain lipids, (there will be a lipid monolayer at this interface), as illustrated in FIG. 1d.

When the monolayer surrounding the droplet 16 contacts the monolayer at the interface 22 between the upper organic phase 20 and the lower aqueous phase 24, a lipid bilayer will form. The droplet electrode (the pipette 10) and the well electrode 26 are electrically coupled and are on opposed sides of the bilayer. Thus, in one aspect, the bilayer can be measured by applying an electrical current to an electrode and measuring a voltage drop across the bilayer, or by applying a voltage to the electrode and measuring the current through the bilayer. When the measurement of the bilayer or any pores or ion channels incorporated into it is completed, the pipette tip 12 can be withdrawn, the aqueous volume completely ejected, the pipette tip rinsed or discarded, and the process repeated.

As can be appreciated, to automate this method of lipid bilayer formation, two motors can be required. For example a first micro-controlled servo motor can actuate the piston 18 of the pipette 10 and a second micro-controlled servo motor can raise and lower the pipette into the well 25.

2. Lipid Bilayer Formation Using a Pin Tool

Figure 2:
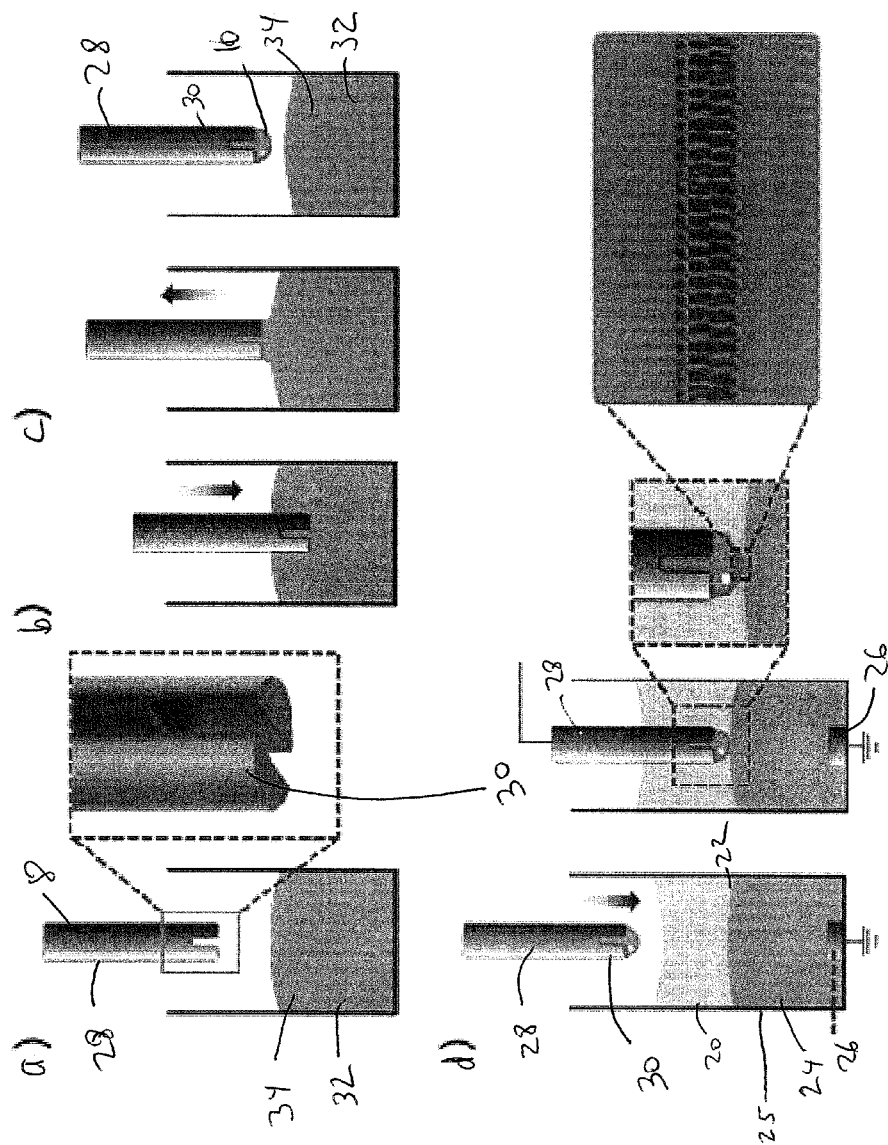
FIG. 2 is a series of cross-sectional views of methods and devices for forming a lipid bilayer, according to one aspect, showing the use of a pin tool.

In certain aspects, the at least a droplet 16 of aqueous solution at the droplet electrode tip can be formed by contacting an aqueous solution. For example, the droplet electrode can comprise a pin tool 28, as illustrated in FIG. 2. In one aspect, the pin tool can be an electrically conductive pin. In another aspect, the pin tool can be a pin on which Ag/AgCl has been deposited to create an Ag/AgCl electrode or a silver pin on which a chloride layer has been deposited to create an Ag/AgCl electrode. As known in the art, pin tools 28 are variations of small cylindrical rods or pins. When the pins are immersed in a solution and withdrawn, surface tension interaction of the pin with the sample solution can cause a small amount of the solution to adhere to the pin. Depending on the size of the pin, surface properties, retraction rate, and other properties, the volume of liquid adherent to the pin can be controllable and repeatable.

In use, a droplet 16 can be formed on the tip 30 of the droplet electrode by, for example, inserting an end of the pin tool 28 into a sample well 32 having an aqueous solution 34 therein, illustrated in FIGS. 2a-2c. Alternatively, a droplet can be formed on the tip of the droplet electrode by, for example, contacting the lower aqueous phase 24 of the well 25 and extracting a droplet of aqueous solution before the upper organic phase 20 is positioned in the well. As the pin is removed from the aqueous phase, a small droplet can hang from the tip 30 of the pin. The droplet 16 of the aqueous solution, which can contain lipid vesicles, can be inserted into the organic phase 20 of the well, and a lipid monolayer will form at the droplet/organic phase interface. The pin can then be lowered until the droplet makes contact with the lower interface 22 occurring between the upper organic phase 20 and the lower aqueous phase 24 which can contain lipids (there will be a lipid monolayer at this interface), as illustrated in FIG. 2d.

When the monolayer surrounding the droplet 16 contacts the monolayer at the interface 22 between the upper organic phase 20 and lower aqueous phase 24, a lipid bilayer will form. The droplet electrode (the pin tool 28) and the well electrode 26 are electrically coupled and are on opposed sides of the bilayer. Thus, in one aspect, the bilayer can be measured by applying an electrical current to an electrode and measuring a voltage drop across the bilayer or by applying a voltage to the electrode and measuring the current through the bilayer. When the measurement of the bilayer or any ion channels incorporated into it is completed, the pin tool can be withdrawn from the well 25, rinsed off, and the process repeated.

In one aspect, to automate this method of lipid bilayer formation, one motor is required to raise and lower the pin tool 28 into the well 25 and the sample well 32.

C. Measuring Current Through a Lipid Bilayer

Also disclosed are methods for measuring current through a bilayer. In one aspect, the method for measuring current comprises providing a droplet electrode. In another aspect, the droplet electrode comprises a pin tool, wherein the tool comprises an electrode and contains an aqueous solution and lipid vesicles. In a further aspect, a well is provided that comprises a lower aqueous phase and an upper organic phase, wherein the lower aqueous phase comprises an electrode and also comprises lipid vesicles. In still a further aspect, the method comprises inserting the pin tool into the well so that a bilayer forms between the lower aqueous phase of the well and the aqueous solution of the pin tool, and measuring the current through the bilayer.

In one aspect, the aqueous solution can be a sessile droplet extracted from the aqueous phase by the pin tool. In a further aspect, the aqueous solution can be contained within an internal reservoir capable of extruding a droplet, such as for example and without limitation, a pipette. In still a further aspect, aqueous solution can be extruded from the internal reservoir, thereby forming a sessile droplet on the silver pin tool.

After formation of a lipid bilayer by any of the methods disclosed herein, the bilayer can be measured. In one aspect, both of the positive displacement pipette and the pin tool systems can use electrodes, such as Ag/AgCl electrodes, placed on both sides of the bilayer to measure protein activity and bilayer formation. In one aspect, the well electrode can be a grounding electrode positioned in the well. The droplet electrode can be, for example, a piston coated with Ag/AgCl. Alternatively, the droplet electrode can be an Ag/AgCl-coated pin. In use, a current or voltage can be applied to the droplet electrode. Electrical measurements can be made, amplified, and digitized to indicate ion channel presence or to measure the bilayer and solution properties.

D. High-Throughout Lipid Bilayer Production

A high-throughput lipid bilayer production device is provided, according to various aspects. In one aspect, the high-throughput lipid bilayer production device comprises a plurality of wells, each well having a well electrode positioned within. In a further aspect, the device can further comprise a droplet electrode electrically coupled to each well electrode and positioned for insertion into any of the plurality of wells. In still a further aspect, the droplet electrode can comprise a tip capable of extracting a droplet of liquid, or an internal reservoir capable of extruding a droplet of liquid. For example, the droplet electrode can comprise an Ag/AgCl pin tool. Alternatively, the droplet electrode can comprise a pipette having a piston coated with Ag/AgCl.

In a further aspect, the high-throughput lipid bilayer production device further comprises a means for positioning 40 the droplet electrode for insertion into a selected well. For example, the means for positioning could be a robotic positioning device or other factory automation positioner. In one aspect, the means for positioning 40 can be a motion control platform of a computer numeric control (CNC) machine, illustrated in FIG. 1.

In one aspect, at least one well of the plurality of wells can further comprise an upper organic phase and a lower aqueous phase in contact with the well electrode, wherein the lower aqueous phase and/or the upper organic phase comprise lipids. For example, at least one well could contain the lower aqueous phase comprising liposomes that can form a lipid monolayer when contacted with the upper organic phase.

Figure 3:
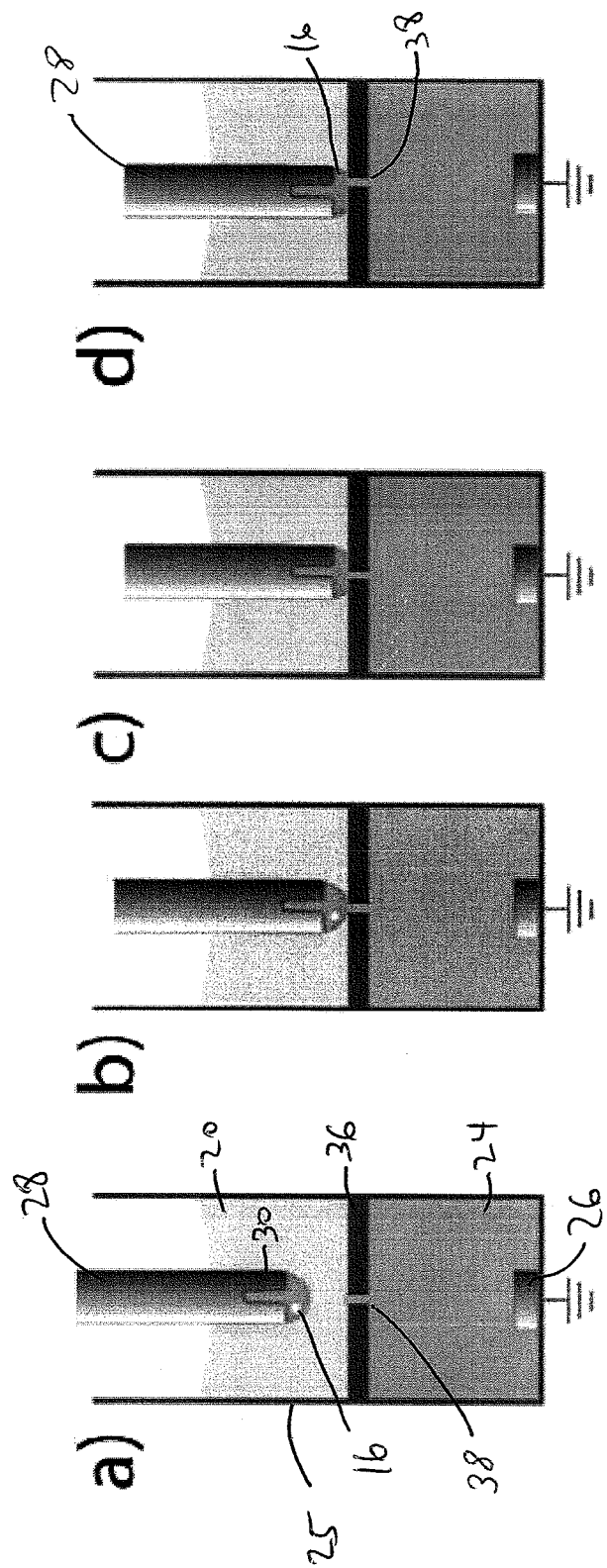
FIG. 3 is a series of cross-sectional views of methods and devices for forming a lipid bilayer, according to one aspect, showing the use of a pin tool and a membrane mask.

In one aspect, at least one well 25 of the plurality of wells can further comprise a membrane mask 36 positioned within the well, illustrated in FIG. 3. In this aspect, the membrane mask can be a mask than can form a barrier between the upper organic phase 20 and the lower aqueous phase 24. In a further aspect, the membrane mask can define a mask aperture 38 that can allow fluid communication between the upper organic phase and the lower aqueous phase. In still a further aspect, the mask aperture can have a diameter less than a diameter of the droplet 16, such that when the droplet is placed in contact with the mask aperture 38, the droplet completely overlies the aperture.

In one aspect, at least one well of the plurality of wells can further comprise an upper organic phase, a lower aqueous phase in contact with the well electrode, and a membrane mask positioned within the well at the interface between the upper organic phase and the lower aqueous phase.

1. Electrode Assemblies for Use in High-Throughout Lipid Bilayer Production Also disclosed are electrode assemblies for use in high-throughput lipid bilayer production. As illustrated in FIG. 1, in one aspect, the electrode assembly comprises an electrode carriage 42 and a means for positioning the carriage 40, a droplet electrode 8 mounted on the carriage and a well electrode 26 electrically coupled to the droplet electrode and mounted on the carriage. In a further aspect, the droplet electrode 8 can have a tip 12 capable of extracting a droplet 16 of liquid, or an internal reservoir 14 capable of extruding a droplet of liquid.

In one aspect, the droplet electrode further comprises a sessile droplet 16 of aqueous solution positioned at the tip of the droplet electrode. In one aspect, the droplet electrode comprises a silver/silver chloride electrode. In one aspect, the droplet electrode comprises a pin tool 28. In one aspect, the droplet electrode tip is capable of extracting a droplet of liquid. In one aspect, the droplet electrode has an internal reservoir capable of extruding a droplet of liquid.

2. Well Arrays for Use in High-Throughput Lipid Bilayer Production

Figure 4:
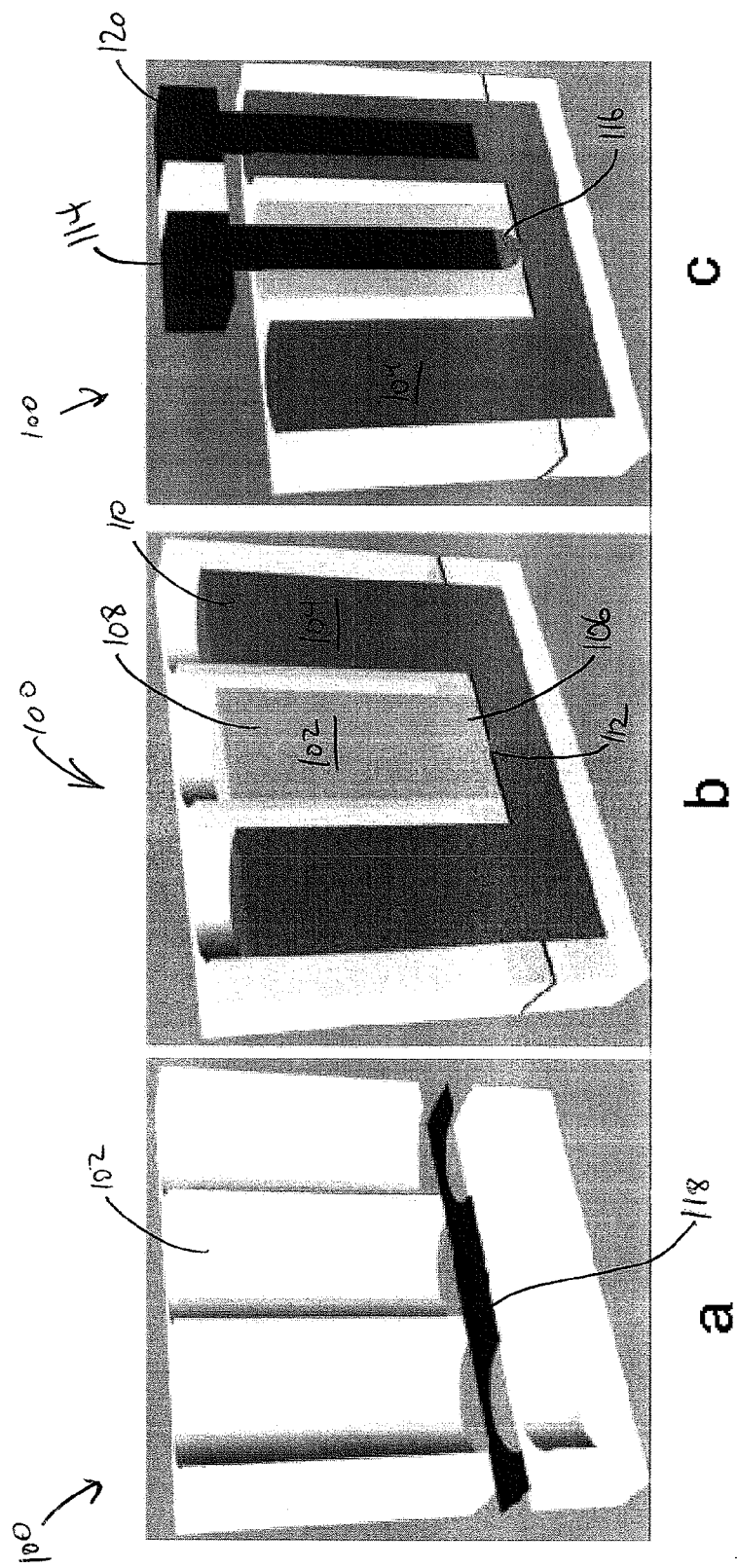
FIG. 4 is a series of cross-sectional views of a device for forming a lipid bilayer, according to one aspect, wherein the device comprises a well comprising multiple chambers.

Also disclosed are well arrays for use in high-throughput lipid bilayer production. In one aspect, the well array comprises a plurality of wells. As illustrated in FIG. 4, in a further aspect each well comprises an organic phase chamber 102, an aqueous phase chamber 104 spaced apart from, but connected to, the organic phase chamber, and optionally, a membrane mask at the connection between the aqueous phase chamber and the organic phase chamber. By "spaced apart from, but connected to," it is meant that the respective chambers allow contact (i.e., an interfacial region) between the aqueous phase and the organic phase (e.g., at the location of lipid bilayer formation and optional mask). Alternatively, the invention can comprise a plurality of spaced apart and separate wells, each well comprising an organic phase chamber 102, an aqueous phase chamber 104 spaced apart from, but connected to, the organic phase chamber, and optionally, a membrane mask at the connection between the aqueous phase chamber and the organic phase chamber.

In one aspect, the organic phase chamber 102 can be a chamber having a predetermined depth that is less than a depth of the aqueous phase chamber 104. An open lower end 106 of the organic phase chamber can optionally be separated from the aqueous phase chamber by the membrane mask. In one aspect, an organic phase 108 can be positioned within the organic phase chamber, and an aqueous phase 110 can be positioned within the aqueous phase chamber. A membrane mask aperture 112 can allow fluid communication between the aqueous phase chamber and the organic phase chamber.

In use, a droplet electrode 114 with a droplet 116 attached thereto can be positioned within the organic phase 108 of the organic phase chamber 102 and lowered to the open lower end 106 of the organic phase chamber. The droplet can contact the aqueous phase and a lipid bilayer can be formed. Optionally, if a membrane mask 118 is present, the droplet can contact the aqueous phase through the membrane mask aperture 112 and a lipid bilayer can be formed. In one aspect, the well electrode 120 can be a pin inserted into the aqueous phase chamber 104. Because the aqueous phase chamber can be spaced apart from the organic phase chamber 102, the well electrode can also be spaced from the organic phase chamber. For example and as illustrated in FIG. 4c, each well can allow top electrode access.

In still a further aspect, the organic phase 108 and the aqueous phase 110 can be substantially immiscible but in contact at the connection between the aqueous phase chamber 104 and the organic phase chamber 102. That is, though the organic phase and the aqueous phase can be in contact with each other, they remain substantially unmixed from each other. In this aspect, the aqueous phase 110 and/or the organic phase 108 comprise lipids, and the sample well 100 can further comprise a droplet electrode 114 having a tip capable of extracting a droplet of liquid or an internal reservoir capable of extruding a droplet of liquid and a well electrode 120 in electrical communication with the droplet electrode.

In one aspect, the droplet electrode 114 further comprises a sessile droplet 116 of aqueous solution positioned at the tip of the droplet electrode.

In one aspect, a high-throughput lipid bilayer production device is provided comprising an electrode assembly and at least two sample wells of a sample well array. For example, a high-throughput lipid bilayer production device can comprise an electrode carriage and a means for positioning the carriage, a droplet electrode mounted on the carriage and a well electrode electrically coupled to the droplet electrode and mounted on the carriage. In a further aspect, the droplet electrode can have a tip capable of extracting a droplet of liquid, or an internal reservoir capable of extruding a droplet of liquid.

E. Formation of Multiple Lipid Bilayers

In one aspect, devices and methods for preparing multiple lipid bilayers are provided.

1. Serial Formation of Multiple Lipid Bilayers

For example, in one aspect, the method for forming a lipid bilayer comprises the steps of providing a droplet electrode with a tip having at least a droplet of aqueous solution, and providing a first well. In a further aspect, the first well comprises an upper organic phase, a lower aqueous phase, and a well electrode extending into the lower aqueous phase. In this aspect, at least one of the aqueous solution, the lower aqueous phase, and the upper organic phase comprise lipids. Also in this aspect, the well electrode and the droplet electrode can be electrically coupled. In a further aspect, the method for forming a lipid bilayer further comprises inserting the droplet electrode into the first well so that a lipid bilayer forms between the lower aqueous phase of the well and the aqueous solution of the droplet electrode tip.

In a further aspect, the method for forming a lipid bilayer further comprises removing the droplet electrode from the first well and moving the droplet electrode to a position for insertion into a second well. In still a further aspect, a sessile droplet of a second aqueous solution can be provided at the droplet electrode tip. In this aspect, the second well comprises a second upper organic phase, a second lower aqueous phase, and a second well electrode in electrical communication with the droplet electrode and extending into the second lower aqueous phase. In a further aspect, the method for forming a lipid bilayer further comprises inserting the droplet electrode into the second well so that a second lipid bilayer forms between the second lower aqueous phase and the second aqueous solution. As can be appreciated, any number of wells can be added and the droplet electrode can be successively inserted into the wells for the formation of a plurality of lipid bilayers.

2. Parallel Formation of Multiple Lipid Bilayers

In one aspect, the method for forming a lipid bilayer comprises the steps of providing a plurality of droplet electrodes, with each droplet electrode having a tip having at least a sessile droplet of aqueous solution. In a further aspect, the method for forming a lipid bilayer further comprises providing a plurality of wells forming a well array. In a further aspect, each well of the plurality of wells comprises an upper organic phase, a lower aqueous phase, and a well electrode extending into the lower aqueous phase. In this aspect, at least one of the aqueous solution, the lower aqueous phase, and the upper organic phase comprise lipids. Also in this aspect, the well electrodes and the droplet electrodes can be electrically coupled.

Figure 6:
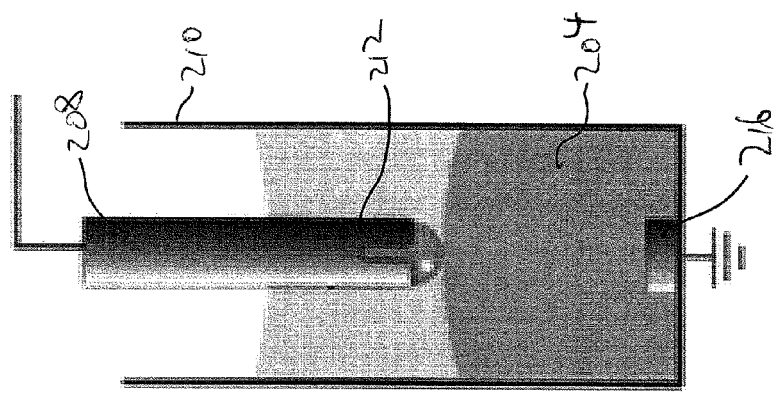
FIG. 6 is a cross-sectional view of methods and devices for forming a plurality of lipid bilayers (e.g., an array), according to one aspect of the invention.
Figure 6:
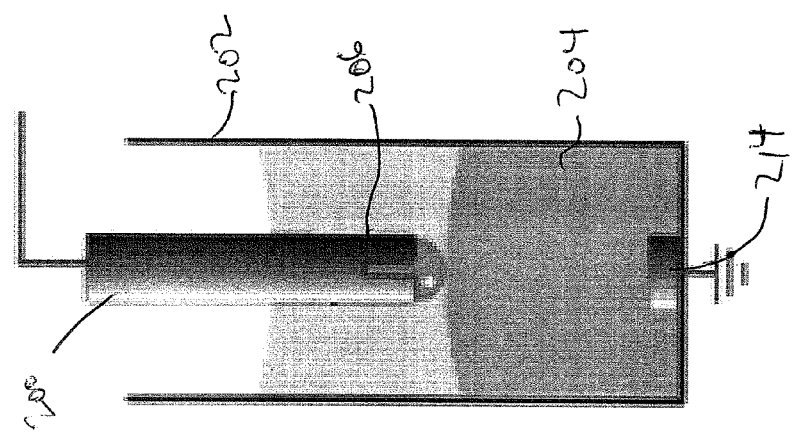

For example, as illustrated in FIG. 6, a plurality of lipid bilayers can be formed by inserting a first droplet electrode 200 into a first well 202 so that a first lipid bilayer forms between the lower aqueous phase 204 of the first well and the aqueous solution of the first droplet electrode tip 206. A second droplet electrode 208 can be inserted into a second well 210 so that a second lipid bilayer forms between the lower aqueous phase 204 of the second well and the aqueous solution of the second droplet electrode tip 212. The first droplet electrode 200 can be electrically coupled to a first well electrode 214, and the second droplet electrode 208 can be electrically coupled to a second well electrode 216 for the measurement of the bilayer formed in each well 202, 210. In one aspect, any number of wells can be added to the well array, and number of droplet electrodes can be utilized for the formation of a plurality of lipid bilayers. Further, as can be appreciated, the formation of a plurality of lipid bilayers can happen simultaneously in the plurality of wells.

F. Experimental

1. Well Preparation

Solutions for lipid bilayer formation and measurement were placed in standard hydrophobic 384 well plates (Fisher Scientific). These wells were modified by drilling a 500 µm hole in the bottom and inserting a 200 µm silver wire (Ted Pella) through the hole and sealing it with Dow Corning 732 sealant. The silver wire was chloridized by placing 70 µl of Clorox bleach in the well for approximately 1 min and thoroughly rinsing the well with DI water. Aqueous solutions placed in the hydrophobic wells produced convex menisci; this allowed for a looser tolerance in the positioning of the upper aqueous droplets and minimized the size of the lipid bilayers formed using both the positive displacement pipette system and the pin tool system. Although bilayers could also be formed in hydrophilic wells, such wells produced concave menisci, and control of the sessile droplet position and bilayer area was experimentally found to be more difficult.

In preparation for artificial bilayer formation, 80 µl of an aqueous measurement buffer MB (1 M KCl, 10 mM Tris-HCl, 1 mM EDTA at pH 8.0) was first deposited into a sample well and 30 µl of MB was added to a measurement well. Next, 40 µl of 5% (w/v) 1,2-diphytanoyl-sn-glycero-3-phosphatidylcholine (DPhPC) (Avanti Polar Lipids) in n-decane (MP Biomedicals) was deposited directly on top of the MB solution in the measurement well, on which it floated, forming a lipid monolayer.

2. Positive Displacement Pipette

Positive displacement pipette tips containing gold plated pistons (NanoEnTek, Inc.) were used with a positive displacement pipette (Microman, Gilson), allowing electrical contact to the fluid contained within the pipette tip through a wire connected to the metal shaft of the pipette plunger. The tip of this gold plated piston was coated with a small amount of Ag/AgCl ink (Ercon) to enable measurement of ionic currents.

To form lipid bilayers with the positive displacement pipette, 0.2 µl of solution from the sample well was withdrawn into the pipette. The pipette tip was then inserted into the organic phase in the measurement well above the organic/aqueous interface and the pipette plunger was depressed partially to form a sessile droplet of MB on the tip of the pipette. At this point, a bilayer could be formed by either lowering the pipette until the lower interface was contacted by the sessile droplet, or further depressing the plunger, growing the sessile droplet until the lower interface was contacted. Ion channels were incorporated into this bilayer by including 100 pg ml$^{-1}$ of Gramicidin A (gA) in the decane phase; electrical activity of gA dimers was observed immediately after bilayer formation.

The process of lipid bilayer formation with the positive displacement pipette was also controlled and automated utilizing the motion control platform of a computer numerical control (CNC) machine (MAXNC15CL, MAXNC). A custom jig was attached to the vertical motion axis of the CNC machine which held the pipette and a servo motor (HS-322HD Deluxe, Hitec) controlled by a microcontroller (ATMega168, Atmel) to depress the pipette plunger.

The sample and measurement wells were pre-filled with solution as described above. The CNC machine was programmed to move the stage so that the pipette was positioned over the sample well. The servo motor then depressed the plunger and the CNC lowered the pipette tip into the sample well to a depth of approximately 4 mm. The servo motor was then activated, partially retracting the plunger and withdrawing 0.2 µl of the sample solution into the pipette tip. The CNC then raised the pipette and moved the stage so that the pipette was positioned above the measurement well. The CNC then lowered the pipette tip 3 mm, leaving it in the upper lipid solution but above the aqueous/organic interface. During a timing delay in the motion control, the servo was activated to depress the plunger and produce a small aqueous droplet hanging from the bottom of the pipette tip. This droplet did not contact the lower aqueous phase and was held above it for a 5 min monolayer stabilization period before final contact. Then the CNC lowered the pipette 1 mm further, contacting the droplet to the lower aqueous phase, forming a lipid bilayer. To minimize measured noise, the electrodes and solutions were placed inside a Faraday cage on the CNC stage (described below) and the CNC was turned off during measurement; since the machine employs closed-loop positioning, the position and program remained unchanged after switching the power on and off.

3. Pin Tools

Silver-silver chloride pins were fabricated from 16 gauge deadsoft silver wire (0.999 purity from C.C. Silver & Gold Inc). The pins were cut to a length of approximately 1 inch and an electrical discharge machine was used to cut slots into the pins and create a flat tip surface. The final slot dimensions were 0.05 inches long and 0.015 inches wide. Prior to use, all of the silver pins were immersed in bleach for approximately 1 minute to create an Ag/AgCl tip, followed by a through rinse in DI water.

Bilayer formation with the silver pin was accomplished using the same measurement and sample well solutions described above, except that the aqueous solutions in the measurement and sample well contained liposomes made from DPhPC and the organic phase contained no lipids. The liposomes were made by dissolving 5 mg of DPhPC in 1 ml of chloroform (Sigma) in a test tube and subsequently evaporating the chloroform under vacuum for 3 hours. 2.5 ml of MB was added to this solution and vortexed for 10 seconds, followed by five freeze/thaw cycles. This resulting solution was then extruded through a 100 nm hydrophilic syringe filter twice to form ~100 nm diameter liposomes and stored at 4° C.

To acquire a droplet, the chloridized pin was lowered into the sample well to a depth of approximately 10 mm for 1 second and removed. This resulted in a small ~1.1 µl droplet hanging from the end of the pin. To form a bilayer, the pin with hanging droplet was lowered into the decane solution in the top half of the measurement well. After waiting approximately 1 min for lipid monolayer formation, the pin was lowered further using a micromanipulator until the droplet contacted the lower aqueous phase. Gramicidin A was dissolved in the aqueous solution to a final concentration of 1 pg ml$^{-1}$ for single channel measurements.

4. Electrical Recordings

Both of the positive displacement pipette and the pin tool systems used Ag/AgCl electrodes placed on both sides of the bilayer to measure protein activity and bilayer formation. The grounding electrode in each system was the Ag/AgCl electrode in the bottom of the 384 well plate. In the positive displacement system, the gold plated piston coated with Ag/AgCl was the droplet electrode while in the pin system, the Ag/AgCl pin was the droplet electrode.

Electrical measurements of bilayers and ion channels were made inside custom-built Faraday cages connecting the Ag/AgCl electrodes at the bottom of the measurement well and the positive displacement pipette or pin tool to an Axopatch 200B amplifier (Axon Instruments), which was used to apply a transmembrane potential and measure the resultant ionic current. The signals were digitized with a Digidata 1332A (Axon Instruments) at 5 kHz, filtered in hardware with a 1 kHz Bessel filter, and further filtered with a 30 Hz Bessel filter and analyzed with Clampfit software (Axon Instruments).

5. Results and Discussion

The contacting monolayer method is a robust method which uses mechanical movements for the formation of a biologically functional lipid bilayer. For successful bilayer formation, a stable monolayer at the interface between an organic or oil solution and an aqueous solution can be required. In each of the systems presented here, there was a period of monolayer formation required before successful bilayer formation was accomplished. When the lipid was dissolved in the organic phase the stabilization time was approximately 5 minutes. When the lipid was dissolved into the aqueous phase, as with pin tool bilayer formation, the stabilization time was only a minute. This can be due to the different mobility and solubility of the lipids in the different phases. In both methods, if the droplets were made to contact the lower aqueous phase prior to the monolayer stabilization periods, then the two aqueous phases would either fuse immediately or have low resistance (<1 GΩ) with a lifetime of a few minutes. With these stabilization periods, bilayers with high resistance (>1 GΩ) would typically form in under 5 minutes and have lifetimes of at least several hours.

Figure 5:
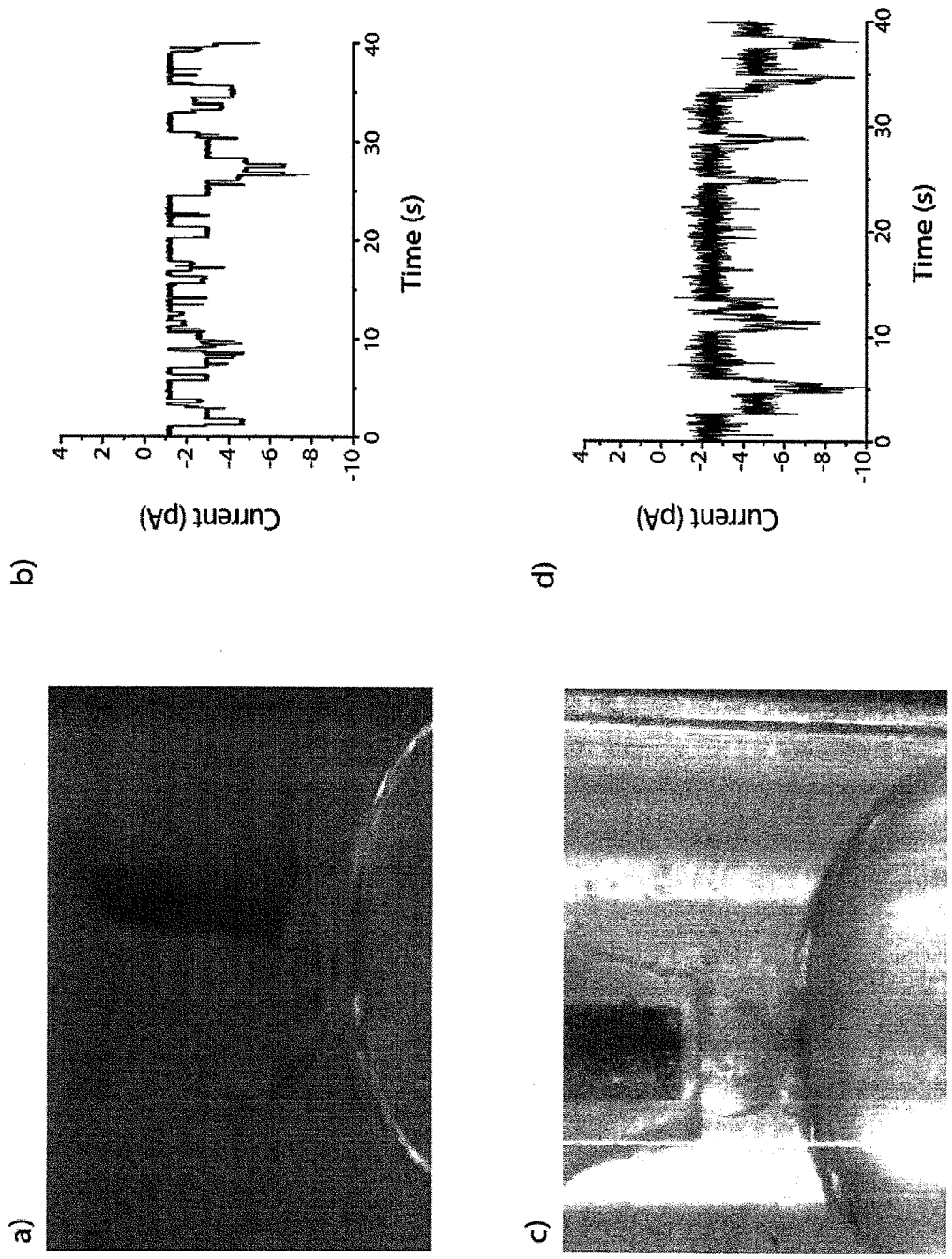
FIGS. 5a and 5c are photographs of a sessile droplet formed by a droplet electrode of a device for forming a lipid bilayer, according to one aspect.
FIGS. 5b and 5d are graphs illustrating the results of an electrical current measured across protein pores incorporated into these lipid bilayers.

Contacting of the two fluidic interfaces could be monitored visually and electrically. In some cases a microscope was used to determine when the droplet interfaces touch, as illustrated in FIGS. 5a and 5c, after which electrical measurements began. Bilayer formation was monitored by measuring the capacitive current resulting from an applied 8 Hz 20 mV (p-p) triangle wave. The capacitance gradually grew and stabilized at a higher value (>100 pF), signifying bilayer formation. This stabilized capacitance could be controlled by changing the droplet contact area through adjustment of the pin or pipette height (100 μm changes in height typically changed the capacitance by 500 pF), see supplementary data, available at stacks.iop.orgaPhysCM/22/454105/mmedia, incorporated herein by reference.

The automated positive displacement pipette platform kept the vertical height of the droplets constant between runs. Servo motor inaccuracies and mechanical slippage between the servo and the pipette plunger head led to errors in fluid handling, resulting in variation in produced droplet size. As a result, there were variations in area of the subsequent bilayers.

In general, bilayers formed from lipids dissolved in the organic phase had a lower resistance than those formed from liposomes in the aqueous phase. Bilayers formed in both systems were able to support single channel measurements of gA, as illustrated in FIGS. 5b and 5d. After bilayer formation, channel incorporation occurred spontaneously and it was observed that the time between the first insertion event and initial bilayers formation depended on protein concentration and bilayer area. In all cases when a bilayer formed in the presence of gA protein, activity was seen. Different numbers of incorporated channels could be obtained by increasing or decreasing the membrane area by controlling the upper droplet height, with higher amounts of protein activity seen with larger bilayers (data not shown).

In general these two methods are similar in nature. Both involve the production and mechanical manipulation of droplets hanging from droplet electrodes to form and measure lipid bilayers. The production of the droplet with the droplet electrode, whether a positive displacement pipette or a pin tool, can be easily accomplished with robotic motion control hardware, and bilayer formation is accomplished with mechanical motion, also amenable to robotic automation. With measurement hardware (e.g. electronic amplifiers) connected to the droplet electrode and an electrode in the well, the lipid bilayer and any ion channels in it can be measured as part of the automation process.

The major difference between these systems is the steps involved in bilayer formation and the location of the lipids for bilayer formation. In the positive displacement system movement of the piston to produce the sessile droplet along with mechanical motion of the droplet electrode are needed to form a bilayer. In the pin tool system, mechanical motion of the electrode is responsible for both fluid handling sessile droplet production and bilayer formation. Mechanical motion controls the volume or size of the droplet hanging from the pin tool. This is because surface tension is the mechanism which causes the pin to carry fluid. Since surface tension is the main mechanism for carrying fluid, the rate of withdrawal from a sample, the depth of submersion, and pin diameter are factors for controlling droplet size. In the positive displacement system the volume of fluid dispensed is controlled by the volume displaced by the piston. Therefore the positive displacement system can require a more precise fluid handling component as well as more precise mechanical motion to bring the droplet and the lower aqueous phase in contact. Alternatively, the pin based system only requires mechanical motion for both precision fluid handling and bilayer formation.

The location of the lipids, either in the aqueous phase or dissolved in the organic phase, can be interchanged between the two systems. In both systems, the lipids can either be loaded in the aqueous phase and/or the organic phase. The positive displacement system can use the lipids dissolved in the organic phase while the pin tool system can use the liposomes in the aqueous phase. Regardless of the mechanical and fluid handling system used, the location of the lipids can have an effect on bilayer resistance and potential applications. Dissolving the liposomes in the organic phase is a very simple process and requires minimal steps. The creation of liposomes requires an addition step, and although not necessarily difficult, requires additional time. Yet when liposomes are used, the creation of asymmetric lipids bilayers is possible (Krylov, "Water Permeability of Asymmetric Planar Lipid Bilayers"). This allows for more control over the biological environment. From a practical standpoint the liposomes are more beneficial for ion channel studies. Typically the reconstitution of ion channels into lipid bilayers involves the isolation and reconstitution of the membrane proteins into lipid vesicles such as liposomes. In an example of these experiments, alpha-hemolysin (aHL) was added directly to the liposome solution and vortexed before use in bilayer formation. The scientific literature contains many examples of ion channel incorporation into liposomes. These channel-containing liposomes can be added to the aqueous solutions to enable the incorporation of these ion channels into the bilayer. Subsequent electrical measurement enables measurement of the conductive properties of the ion channels.

The positive displacement system can be considered a disposable system while the pin tool system can be a reusable bilayer formation system. Pins, commonly used to transfer various pharmaceutical compounds, must be rigorously cleaned between sampling to achieve uniformity and repeatability. In general, these cleaning steps are considered the lowest throughput part of pin tool liquid handling and there are continued efforts to improve this technology. The positive displacement system uses disposable pipette tips and therefore no cleaning is involved. This can allow for high throughput in the future, yet the high cost associated with the use of these tips, especially for future application requiring large numbers of tips, can reduce their potential. Therefore, depending on specific applications, these systems can find individual applications.

Another difference that was noticed by placing the lipids in either the organic or aqueous phases was the resistance of the bilayers. Although the exact mechanism that causes high resistance membranes is not known, it is believed to be due to the lipids participating in the transport of ions across the organic phase or a property of the monolayers used to form bilayers. When a large amount of lipids are present in the organic phase, reverse micelles are able to surround charged ions, reducing the energy required for the ion to be present in the organic phase. These reverse micelles can then travel across the organic phase, producing an ionic current under an applied voltage. When the lipids are present in the aqueous phase, there are fewer lipids available to transport ions across the organic phase, reducing the ionic current. Regardless, the lower resistance did not affect the ability to measure signal channel currents. Both alpha-hemolysin and gramicidin were measured and single channel conductances could be resolved.

The positive displacement fluid handling system provided herein demonstrates the ability to form and measure lipid bilayers, and ion channels incorporated into bilayers, using a fully automated system. This platform can find applications in high-throughput drug screening, as the equipment used is standard in pharmaceutical laboratories. In the context of high-throughput screening, the major bottleneck in this process can be the monolayer stabilization time. Yet, it is possible to scale this system to 1536-well plates, and beyond, with microfluidics. The development of low-noise multichannel amplifiers will allow simultaneous measurements, and can lead to increased throughput. In addition to this, the high level of membrane resistance without precision equipment provides a robust platform for ion channel studies. In addition to applications in drug discovery, the system design allows for a variety of uses, such as remote stochastic sensing, as bilayer formation is automated and no operator is needed for measurements.

The pin tool system provided herein allows standard liquid handling systems to use mechanical motion for bilayer formation. This technique is widely usable and scalable to a 1536-well format. The automation of this system can be easier than the positive displacement system as there is no need for fluid handling since the mechanical motion of the pin determines the volume and size of the droplets. This approach, combined with the positive displacement system automation platform, can yield higher throughput approaches to forming high resistance planar lipid bilayers.

G. Examples

1. Forming a Lipid Bilayer with a Pin Tool

In one example, to form a lipid bilayer, a droplet electrode, such as a pin tool, and a well can be provided. In one aspect, the pin tool can have a tip capable of extracting a sessile droplet of an aqueous solution. In a further aspect, the pin tool can be an electrically conductive pin tool. According to one aspect, the well can have a lower aqueous phase positioned in a lower portion of the well, and an upper organic phase (which has a higher density than the lower aqueous phase), positioned in the well above the lower aqueous phase. A lipid monolayer can be present at the interface between the upper organic phase and the lower aquatic phase. In another aspect, the well can comprise a well electrode electrically coupled to the droplet electrode and that extends into the lower aqueous phase in the well. In this example, at least one of the aqueous solution, the lower aqueous phase, and the upper organic phase comprise lipids.

The droplet electrode, in this example the pin tool, can be placed in contact with an aqueous solution, such as an aqueous solution in a sample well. At least a sessile droplet of the aqueous solution can be formed at the tip of the pin tool upon removal of the tip from the aqueous solution of the sample well. The tip of the pin tool and the sessile droplet of the aqueous solution attached to the tip can be inserted into the well. A lipid monolayer can be formed between the aqueous solution of the sessile droplet and the upper organic phase. After a dwell time to let the monolayer sufficiently develop, the pin tool can be lowered into the organic phase until the sessile droplet contacts the interface between the upper organic phase and the lower aqueous phase of the well. The lipid bilayer can be formed by joining the lipid monolayers formed on the surface of interface and the monolayer of the aqueous solution of the pin tool tip. A current or voltage can be applied to the well electrode or the pin tool and the bilayer can be electrically measured without disturbing the aqueous solution, the lower aqueous phase, or the upper organic phase.

2. Forming a Lipid Bilayer with a Positive Displacement Pipette

In one example, to form a lipid bilayer, a droplet electrode, such as a positive displacement pipette, and a well can be provided. In one aspect, the pipette can have a tip capable of extruding a sessile droplet of an aqueous solution. In a further aspect, the pipette can have an electrically conductive piston. According to one aspect, the well can have a lower aqueous phase positioned in a lower portion of the well, and an upper organic phase (which has a higher density than the lower aqueous phase), positioned in the well above the lower aqueous phase. A lipid monolayer can be present at the interface between the upper organic phase and the lower aquatic phase. In another aspect, the well can comprise a well electrode electrically coupled to the droplet electrode and that extends into the lower aqueous phase in the well. In this example, at least one of the aqueous solution, the lower aqueous phase, and the upper organic phase comprise lipids.

The droplet electrode, in this example the pipette, can be placed in contact with an aqueous solution, such as an aqueous solution in a sample well. A piston of the pipette can be moved to a withdrawn position, and a portion of the aqueous solution in the sample well can be extracted from the aqueous solution into a reservoir of the pipette. Upon removal of the tip of the pipette from the aqueous solution of the sample well, a sessile droplet of the aqueous solution can be formed on the tip by depressing the piston of the pipette. The tip of the pipette and the sessile droplet of the aqueous solution attached to the tip can be inserted into the well. A lipid monolayer can be formed between the aqueous solution of the sessile droplet and the upper organic phase. After a dwell time to let the monolayer sufficiently develop, the pipette can be lowered into the organic phase until the sessile droplet contacts the interface between the upper organic phase and the lower aqueous phase of the well. The lipid bilayer can be formed by joining the lipid monolayers formed on the surface of interface and the monolayer of the aqueous solution of the pipette tip. A current or voltage can be applied to the well electrode and the electrically conductive piston, and the bilayer can be electrically measured without disturbing the aqueous solution, the lower aqueous phase, or the upper organic phase.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A method for forming a lipid bilayer, comprising the steps of:
    a) providing a droplet electrode with a tip having at least a sessile droplet of aqueous solution;
    b) providing a well comprising:
        i) an upper organic phase,
        ii) a lower aqueous phase, and
        iii) a well electrode extending into the lower aqueous phase,
    wherein at least one of the aqueous solution, the lower aqueous phase, and the upper organic phase comprise lipids, and
    wherein the droplet electrode and the well electrode are in electrical communication; and
    c) inserting the droplet electrode into the well so that a lipid bilayer forms between the lower aqueous phase of the well and the aqueous solution of the droplet electrode tip.

2. The method of claim 1, further comprising measuring current through the bilayer by applying a voltage between the droplet electrode and the well electrode.

3. The method of claim 1, further comprising the steps of
    a) removing the droplet electrode from the well;
    b) moving the droplet electrode to a position for insertion into a second well;
    c) providing a sessile droplet of second aqueous solution at the droplet electrode tip;
    wherein the second well comprises a second upper organic phase, a second lower aqueous phase, and a second well electrode in electrical communication with the droplet electrode and extending into the second lower aqueous phase; and
    d) inserting the droplet electrode into the second well so that a second lipid bilayer forms between the second lower aqueous phase and the second aqueous solution.

4. The method of claim 1, wherein the droplet electrode comprises a silver/silver chloride electrode.

5. The method of claim 1, wherein providing a droplet electrode with a tip having at least a sessile droplet of aqueous solution comprises extracting a droplet of aqueous solution from the lower aqueous phase before the upper organic phase is positioned in the well.

6. The method of claim 1, wherein the at least a sessile droplet of aqueous solution at the droplet electrode tip is formed by extrusion from an internal reservoir.

7. A method for measuring current through a bilayer, comprising:
    a) providing a silver pin tool, wherein the tool comprises an electrode and contains an aqueous solution and lipid vesicles;
    b) providing a well, wherein the well comprises a lower aqueous phase and an upper organic phase; wherein the lower aqueous phase comprises an electrode and also comprises lipid vesicles;
    c) inserting the silver pin tool into the well so that a bilayer forms between the lower aqueous phase of the well and the aqueous solution of the pin tool; and
    d) measuring the current through the bilayer.

8. The method of claim 7, wherein the aqueous solution is a sessile droplet extracted from the aqueous phase by the silver pin tool.

9. The method of claim 7, wherein the aqueous solution is contained within an internal reservoir capable of extruding a droplet.

10. A high-throughput lipid bilayer production device comprising:
    a) a plurality of wells, each well having a well electrode positioned within; and
    b) a droplet electrode electrically coupled to each well electrode and positioned for insertion into any of the plurality of wells, the droplet electrode having:
        i) a tip capable of extracting a droplet of liquid, or ii) an internal reservoir capable of extruding a droplet of liquid; wherein at least one well further comprises:
    a) an upper organic phase, and
    b) a lower aqueous phase in contact with the well electrode, wherein the lower aqueous phase and/or the upper organic phase comprise lipids.

11. The device of claim 10, further comprising a means for positioning the droplet electrode for insertion into a selected well.

12. The device of claim 11, wherein the means for positioning is a motion control platform of a computer numeric control (CNC) machine.

13. The device of claim 10, wherein at least one well further comprises a membrane mask positioned within the well.

14. The device of claim 10, wherein at least one well further comprises an upper organic phase, a lower aqueous phase in contact with the well electrode, and a membrane mask positioned within the well at the interface between the upper organic phase and the lower aqueous phase.

15. An electrode assembly for use in high-throughput lipid bilayer production, the electrode assembly comprising:
    a) an electrode carriage and a means for positioning the carriage;
    b) a droplet electrode mounted on the carriage and having a tip capable of extracting a droplet of liquid or an internal reservoir capable of extruding a droplet of liquid; and
    c) a well electrode electrically coupled to the droplet electrode and mounted on the carriage; wherein at least one well further comprises:
    a) an upper organic phase, and
    b) a lower aqueous phase in contact with the well electrode, wherein the lower aqueous phase and/or the upper organic phase comprise lipids.

16. The electrode assembly of claim 15, wherein the droplet electrode further comprises a sessile droplet of aqueous solution positioned at the tip of the droplet electrode.

17. A well array for use in high-throughput lipid bilayer production, the well array comprising a plurality of wells, each well comprising:
    a) an organic phase chamber;
    b) an aqueous phase chamber spaced apart from, but connected to, the organic phase chamber; and
    c) optionally, a membrane mask at the connection between the aqueous phase chamber and the organic phase chamber; wherein at least one well further comprises:
    a) an upper organic phase, and b) a lower aqueous phase in contact with the well electrode, wherein the lower aqueous phase and/or the upper organic phase comprise lipids.

18. A high-throughput lipid bilayer production device comprising:
   a) an electrode assembly comprising:
      i) an electrode carriage and a means for positioning the carriage;
      ii) a droplet electrode mounted on the carriage and having a tip capable of extracting a droplet of liquid or an internal reservoir capable of extruding a droplet of liquid; and
      iii) a well electrode electrically coupled to the droplet electrode and mounted on the carriage; and
   b) a well array comprising a plurality of wells, each well comprising:
      i) an organic phase chamber;
      ii) an aqueous phase chamber spaced apart from, but connected to, the organic phase chamber; and
      iii) optionally, a membrane mask at the connection between the aqueous phase chamber and the organic phase chamber.

19. The device of claim 18, further comprising a second electrode assembly, the device configured to form a lipid bilayer in more than one well simultaneously and in parallel.

* * * * *